(12) United States Patent
Annoni et al.

(10) Patent No.: US 11,751,804 B2
(45) Date of Patent: *Sep. 12, 2023

(54) METHOD AND APPARATUS FOR PAIN MANAGEMENT USING OBJECTIVE PAIN MEASURE

(71) Applicant: Boston Scientific Neuromodulation Corporation, Valencia, CA (US)

(72) Inventors: Elizabeth Mary Annoni, White Bear Lake, MN (US); Bryan Allen Clark, Forest Lake, MN (US); Pramodsingh Hirasingh Thakur, Woodbury, MN (US); Jianwen Gu, Valencia, CA (US); James John Kleinedler, Plymouth, MN (US); Kyle Harish Srivastava, Saint Paul, MN (US); David J. Ternes, Roseville, MN (US); David L. Perschbacher, Coon Rapids, MN (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 401 days.

This patent is subject to a terminal disclaimer.

(21) Appl. No.: 16/986,519

(22) Filed: Aug. 6, 2020

(65) Prior Publication Data
US 2020/0359960 A1 Nov. 19, 2020

Related U.S. Application Data

(63) Continuation of application No. 15/688,676, filed on Aug. 28, 2017, now Pat. No. 10,750,994.
(Continued)

(51) Int. Cl.
*A61B 5/00* (2006.01)
*A61B 5/11* (2006.01)
(Continued)

(52) U.S. Cl.
CPC .......... *A61B 5/4824* (2013.01); *A61B 5/1118* (2013.01); *A61B 5/4836* (2013.01);
(Continued)

(58) Field of Classification Search
CPC ... A61B 5/4824; A61B 5/1118; A61B 5/4836; A61B 5/4848
See application file for complete search history.

(56) References Cited

U.S. PATENT DOCUMENTS

| 4,297,685 A | 10/1981 | Brainard, II |
| 5,187,675 A | 2/1993 | Dent et al. |

(Continued)

FOREIGN PATENT DOCUMENTS

| AU | 2017335497 B2 | 4/2020 |
| AU | 2017334841 B2 | 7/2020 |

(Continued)

OTHER PUBLICATIONS

"2015 Sleep in America® Poll Sleep and Pain—Summary of Findings", National Sleep Foundation, (2015), 1-54.
(Continued)

*Primary Examiner* — Joseph M Dietrich
(74) *Attorney, Agent, or Firm* — Schwegman Lundberg & Woessner, P.A.

(57) ABSTRACT

An example of a system for managing pain may include a pain monitoring circuit, a pain relief device, and a control circuit. The pain monitoring circuit may include a parameter analyzer and a pain score generator. The parameter analyzer may be configured to receive and analyze at least two parameters selected from a physiological parameter indicative of a physiological function or state of a patient, a functional parameter indicative of a physical activity or state of the patient, or a patient parameter including subjective information provided by the patient. The pain score genera-
(Continued)

tor may be configured to compute a composite pain score using an outcome of the analysis. The composite pain score may indicate a degree of the pain. The pain relief device may be configured to deliver a pain-relief therapy. The control circuit may be configured to control the delivery of the pain-relief therapy using the composite pain score.

20 Claims, 7 Drawing Sheets

Related U.S. Application Data

(60) Provisional application No. 62/400,336, filed on Sep. 27, 2016.

(51) Int. Cl.
| | | |
|---|---|---|
| G16H 50/20 | (2018.01) | |
| G16H 20/70 | (2018.01) | |
| G16H 50/30 | (2018.01) | |
| G16H 40/63 | (2018.01) | |

(52) U.S. Cl.
CPC .......... *A61B 5/4848* (2013.01); *A61B 5/7275* (2013.01); *A61B 5/7475* (2013.01); *G16H 20/70* (2018.01); *G16H 40/63* (2018.01); *G16H 50/20* (2018.01); *G16H 50/30* (2018.01); *A61B 2505/07* (2013.01); *A61B 2505/09* (2013.01)

(56) References Cited

U.S. PATENT DOCUMENTS

| | | | |
|---|---|---|---|
| 5,774,591 | A | 6/1998 | Black et al. |
| 6,016,103 | A | 1/2000 | Leavitt |
| 6,076,011 | A | 6/2000 | Hoover |
| 6,088,040 | A | 7/2000 | Oda et al. |
| 6,173,260 | B1 | 1/2001 | Slaney |
| 6,480,734 | B1 | 11/2002 | Zhang et al. |
| 6,497,658 | B2 | 12/2002 | Roizen et al. |
| 6,654,632 | B2 | 11/2003 | Lange et al. |
| 6,659,968 | B1 | 12/2003 | McClure |
| 6,731,984 | B2 | 5/2004 | Cho et al. |
| 6,871,099 | B1 | 3/2005 | Whitehurst et al. |
| 7,001,337 | B2 | 2/2006 | Dekker |
| 7,004,907 | B2 | 2/2006 | Banet et al. |
| 7,177,686 | B1 | 2/2007 | Turcott |
| 7,189,204 | B2 | 3/2007 | Ni et al. |
| 7,222,075 | B2 | 5/2007 | Petrushin |
| 7,299,086 | B2 | 11/2007 | McCabe et al. |
| 7,376,457 | B2 | 5/2008 | Ross |
| 7,407,485 | B2 | 8/2008 | Huiku |
| 7,463,927 | B1 | 12/2008 | Chaouat |
| 7,566,308 | B2 | 7/2009 | Stahmann |
| 7,627,475 | B2 | 12/2009 | Petrushin |
| 7,636,602 | B2 | 12/2009 | Baru Fassio et al. |
| 7,650,184 | B2 | 1/2010 | Walter |
| 7,678,061 | B2 | 3/2010 | Lee et al. |
| 7,775,993 | B2 | 8/2010 | Heruth et al. |
| 7,957,809 | B2 | 6/2011 | Bourget et al. |
| 7,986,991 | B2 | 7/2011 | Prichep |
| 8,019,439 | B2 | 9/2011 | Kuzma et al. |
| 8,055,348 | B2 | 11/2011 | Heruth et al. |
| 8,083,682 | B2 | 12/2011 | Dalal et al. |
| 8,192,376 | B2 | 6/2012 | Lovett et al. |
| 8,209,182 | B2 | 6/2012 | Narayanan |
| 8,290,596 | B2 | 10/2012 | Wei et al. |
| 8,332,038 | B2 | 12/2012 | Heruth et al. |
| 8,398,556 | B2 | 3/2013 | Sethi et al. |
| 8,447,401 | B2 | 5/2013 | Miesel et al. |
| 8,475,370 | B2 | 7/2013 | McCombie et al. |
| 8,529,459 | B2 | 9/2013 | Malker et al. |
| 8,606,356 | B2 | 12/2013 | Lee et al. |
| 8,688,221 | B2 | 4/2014 | Miesel |
| 8,744,587 | B2 | 6/2014 | Miesel et al. |
| 8,805,518 | B2 | 8/2014 | King et al. |
| 9,066,659 | B2 | 6/2015 | Thakur et al. |
| 9,072,870 | B2 | 7/2015 | Wu et al. |
| 9,119,965 | B2 | 9/2015 | Xi et al. |
| 9,314,168 | B2 | 4/2016 | Watson et al. |
| 9,395,792 | B1 | 7/2016 | Kahn et al. |
| 10,349,212 | B2 | 7/2019 | Tartz et al. |
| 10,610,688 | B2 | 4/2020 | Thakur et al. |
| 10,631,776 | B2 | 4/2020 | Annoni et al. |
| 10,631,777 | B2 | 4/2020 | Clark et al. |
| 10,667,747 | B2 | 6/2020 | Annoni et al. |
| 10,675,469 | B2 | 6/2020 | Annoni et al. |
| 10,729,905 | B2 | 8/2020 | Annoni et al. |
| 10,750,994 | B2 | 8/2020 | Annoni et al. |
| 10,898,718 | B2 | 1/2021 | Srivastava et al. |
| 10,926,091 | B2 | 2/2021 | Srivastava et al. |
| 10,960,210 | B2 | 3/2021 | Srivastava et al. |
| 11,337,646 | B2 | 5/2022 | Annoni et al. |
| 11,395,625 | B2 | 7/2022 | Clark et al. |
| 11,439,827 | B2 | 9/2022 | Srivastava et al. |
| 11,446,499 | B2 | 9/2022 | Thakur et al. |
| 2001/0037222 | A1 | 11/2001 | Platt et al. |
| 2002/0042563 | A1 | 4/2002 | Becerra et al. |
| 2004/0015091 | A1 | 1/2004 | Greenwald et al. |
| 2005/0010262 | A1 | 1/2005 | Sharan et al. |
| 2005/0209643 | A1 | 9/2005 | Heruth et al. |
| 2007/0167859 | A1 | 7/2007 | Finneran et al. |
| 2007/0213783 | A1 | 9/2007 | Pless |
| 2007/0260285 | A1 | 11/2007 | Libbus et al. |
| 2008/0015659 | A1 | 1/2008 | Zhang et al. |
| 2008/0077192 | A1 | 3/2008 | Harry et al. |
| 2008/0177191 | A1 | 7/2008 | Patangay et al. |
| 2008/0249430 | A1 | 10/2008 | John et al. |
| 2009/0124863 | A1 | 5/2009 | Liu et al. |
| 2009/0192556 | A1 | 7/2009 | Wu et al. |
| 2009/0312663 | A1 | 12/2009 | John et al. |
| 2009/0318986 | A1 | 12/2009 | Alo et al. |
| 2010/0016913 | A1 | 1/2010 | Arcot-Krishnamurthy et al. |
| 2010/0105997 | A1 | 4/2010 | Ecker et al. |
| 2010/0191311 | A1 | 7/2010 | Scheiner et al. |
| 2010/0286549 | A1 | 11/2010 | John et al. |
| 2011/0015702 | A1 | 1/2011 | Ternes et al. |
| 2011/0021928 | A1 | 1/2011 | Giovangrandi et al. |
| 2011/0034760 | A1 | 2/2011 | Brynelsen et al. |
| 2011/0112420 | A1 | 5/2011 | Nagata et al. |
| 2011/0124979 | A1 | 5/2011 | Heneghan et al. |
| 2011/0137134 | A1 | 6/2011 | Hemmerling et al. |
| 2011/0172562 | A1 | 7/2011 | Sahasrabudhe et al. |
| 2011/0224749 | A1 | 9/2011 | Ben-David et al. |
| 2011/0306846 | A1 | 12/2011 | Osorio |
| 2012/0046715 | A1 | 2/2012 | Moffitt et al. |
| 2012/0109012 | A1 | 5/2012 | Cinbis |
| 2012/0150545 | A1 | 6/2012 | Simon |
| 2012/0277818 | A1 | 11/2012 | Stancer et al. |
| 2013/0066394 | A1 | 3/2013 | Saab |
| 2013/0165994 | A1 | 6/2013 | Ternes et al. |
| 2013/0211291 | A1 | 8/2013 | Tran |
| 2013/0268016 | A1 | 10/2013 | Xi et al. |
| 2014/0276188 | A1 | 9/2014 | Jardin |
| 2014/0276549 | A1 | 9/2014 | Osorio |
| 2014/0309709 | A1 | 10/2014 | Gozani et al. |
| 2015/0005842 | A1 | 1/2015 | Lee et al. |
| 2015/0025335 | A1 | 1/2015 | Jain et al. |
| 2015/0148878 | A1 | 5/2015 | Yoo et al. |
| 2015/0289803 | A1 | 10/2015 | Wu et al. |
| 2016/0022203 | A1 | 1/2016 | Arnold et al. |
| 2016/0082265 | A1 | 3/2016 | Moffitt et al. |
| 2016/0129272 | A1 | 5/2016 | Hou et al. |
| 2016/0144194 | A1 | 5/2016 | Roothans et al. |
| 2016/0158551 | A1 | 6/2016 | Kent et al. |
| 2016/0198996 | A1 | 7/2016 | Dullen |
| 2016/0243359 | A1 | 8/2016 | Sharma |
| 2016/0302720 | A1 | 10/2016 | John et al. |
| 2016/0350509 | A1 | 12/2016 | Sharma |
| 2016/0361515 | A1 | 12/2016 | Jung et al. |
| 2016/0374567 | A1 | 12/2016 | Breslow et al. |
| 2017/0128722 | A1 | 5/2017 | Perez |

(56) References Cited

U.S. PATENT DOCUMENTS

| | | |
|---|---|---|
| 2017/0136264 A1 | 5/2017 | Hyde et al. |
| 2017/0164876 A1 | 6/2017 | Hyde et al. |
| 2017/0165485 A1 | 6/2017 | Sullivan et al. |
| 2018/0078768 A1 | 3/2018 | Thakur et al. |
| 2018/0085055 A1 | 3/2018 | Annoni et al. |
| 2018/0085584 A1 | 3/2018 | Thakur et al. |
| 2018/0110464 A1 | 4/2018 | Annoni et al. |
| 2018/0126169 A1 | 5/2018 | Hou et al. |
| 2018/0192941 A1 | 7/2018 | Annoni et al. |
| 2018/0192942 A1 | 7/2018 | Clark et al. |
| 2018/0192943 A1 | 7/2018 | Annoni et al. |
| 2018/0193644 A1 | 7/2018 | Annoni et al. |
| 2018/0193650 A1 | 7/2018 | Srivastava et al. |
| 2018/0193651 A1 | 7/2018 | Annoni et al. |
| 2018/0193652 A1 | 7/2018 | Srivastava et al. |
| 2018/0229040 A1 | 8/2018 | Srivastava et al. |
| 2019/0022397 A1 | 1/2019 | Srivastava et al. |
| 2020/0188673 A1 | 6/2020 | Thakur et al. |
| 2020/0214623 A1 | 7/2020 | Annoni et al. |
| 2020/0214624 A1 | 7/2020 | Clark et al. |
| 2020/0238087 A1 | 7/2020 | Annoni et al. |
| 2021/0060343 A1 | 3/2021 | Srivastava et al. |
| 2021/0128921 A1 | 5/2021 | Srivastava et al. |
| 2021/0178164 A1 | 6/2021 | Srivastava et al. |
| 2022/0323760 A1 | 10/2022 | Thakur et al. |
| 2022/0379119 A1 | 12/2022 | Srivastava et al. |

FOREIGN PATENT DOCUMENTS

| | | |
|---|---|---|
| EP | 1059064 A2 | 12/2000 |
| EP | 1897586 A1 | 3/2008 |
| EP | 3519037 B1 | 7/2020 |
| EP | 3568069 B1 | 4/2021 |
| EP | 3518736 B1 | 8/2021 |
| RU | 2559783 C1 | 8/2015 |
| WO | WO-2007007058 A1 | 1/2007 |
| WO | WO-2009055127 A1 | 4/2009 |
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | WO-2014151860 A1 | 9/2014 |
| WO | WO-2015060888 A1 | 4/2015 |
| WO | WO-2015128567 | 9/2015 |
| WO | WO-2016025989 A1 | 2/2016 |
| WO | WO-2016077786 A1 | 5/2016 |
| WO | WO-2018052695 A1 | 3/2018 |
| WO | WO-2018063637 A1 | 4/2018 |
| WO | WO-2018063912 A1 | 4/2018 |
| WO | WO-2018080887 A1 | 5/2018 |
| WO | WO-2019018206 A1 | 1/2019 |

OTHER PUBLICATIONS

"U.S. Appl. No. 15/687,925, Final Office Action dated Feb. 14, 2019", 10 pgs.

"U.S. Appl. No. 15/687,925, Non Final Office Action dated Jun. 11, 2019", 11 pgs.

"U.S. Appl. No. 15/687,925, Non Final Office Action dated Oct. 9, 2018", 9 pgs.

"U.S. Appl. No. 15/687,925, Response filed Jan. 9, 2019 to Non Final Office Action dated Oct. 9, 2018", 9 pgs.

"U.S. Appl. No. 15/687,925, Response filed May 13, 2019 to Final Office Action dated Feb. 14, 2019", 11 pgs.

"U.S. Appl. No. 15/688,676, Examiner Interview Summary dated Sep. 25, 2019", 3 pgs.

"U.S. Appl. No. 15/688,676, Final Office Action dated Jul. 29, 2019", 7 pgs.

"U.S. Appl. No. 15/688,676, Non Final Office Action dated Jan. 11, 2019", 7 pgs.

"U.S. Appl. No. 15/688,676, Non Final Office Action dated Oct. 30, 2019", 6 pgs.

"U.S. Appl. No. 15/688,676, Notice of Allowance dated Apr. 14, 2020", 7 pgs.

"U.S. Appl. No. 15/688,676, Response filed Jan. 7, 2020 to Non Final Office Action dated Oct. 30, 2019", 10 pgs.

"U.S. Appl. No. 15/688,676, Response filed Sep. 25, 2019 to Final Office Action dated Jul. 29, 2019", 10 pgs.

"U.S. Appl. No. 15/688,676, Response filed Apr. 9, 2019 to Non Final Office Action dated Jan. 11, 2019", 12 pgs.

"U.S. Appl. No. 15/711,578, Examiner Interview Summary dated Aug. 28, 2019", 3 pgs.

"U.S. Appl. No. 15/711,578, Non Final Office Action dated May 23, 2019", 6 pgs.

"U.S. Appl. No. 15/711,578, Notice of Allowance dated Nov. 25, 2019", 7 pgs.

"U.S. Appl. No. 15/711,578, Repsonse filed Aug. 23, 2019 to Non Final Office Action dated May 23, 2019", 11 pgs.

"U.S. Appl. No. 15/711,578, Supplemental Response filed Aug. 28, 2019 to Non Final Office Action dated May 23, 2019", 11 pgs.

"U.S. Appl. No. 15/788,403, Non Final Office Action dated Jul. 23, 2019", 9 pgs.

"U.S. Appl. No. 15/788,403, Response filed Oct. 8, 2019 to Non Final Office Action dated Jul. 23, 2019", 11 pgs.

"U.S. Appl. No. 15/867,756, Examiner Interview Summary dated Aug. 28, 2019", 3 pgs.

"U.S. Appl. No. 15/867,756, Non Final Office Action dated Jul. 1, 2019", 8 pgs.

"U.S. Appl. No. 15/867,756, Notice of Allowance dated Dec. 19, 2019", 7 pgs.

"U.S. Appl. No. 15/867,756, Response filed Aug. 29, 2019 to Non Final Office Action dated Jul. 1, 2019", 11 pgs.

"U.S. Appl. No. 15/867,760, Examiner Interview Summary dated Aug. 28, 2019", 3 pgs.

"U.S. Appl. No. 15/867,760, Non Final Office Action dated Jul. 1, 2019", 8 pgs.

"U.S. Appl. No. 15/867,760, Notice of Allowance dated Dec. 19, 2019", 7 pgs.

"U.S. Appl. No. 15/867,760, Response filed Aug. 29, 2019 to Non-Final Office Action dated Jul. 1, 2019", 11 pgs.

"U.S. Appl. No. 15/867,767, Non Final Office Action dated Dec. 17, 2019", 11 pgs.

"U.S. Appl. No. 15/867,801, Non Final Office Action dated Sep. 30, 2019", 10 pgs.

"U.S. Appl. No. 15/867,801, Response filed Dec. 18, 2019 to Non Final Office Action dated Sep. 30, 2019", 12 pgs.

"U.S. Appl. No. 15/888,808, Examiner Interview Summary dated Nov. 21, 2019", 3 pgs.

"U.S. Appl. No. 15/888,808, Final Office Action dated Dec. 16, 2019", 7 pgs.

"U.S. Appl. No. 15/888,808, Non Final Office Action dated Sep. 11, 2019", 7 pgs.

"U.S. Appl. No. 15/888,808, Response filed Nov. 19, 2019 to Non Final Office Action dated Sep. 11, 2019", 10 pgs.

"Australian Application Serial No. 2017325823, First Examination Report dated Jun. 19, 2019", 3 pgs.

"Australian Application Serial No. 2017334841, First Examination Report dated Jun. 24, 2019", 3 pgs.

"Australian Application Serial No. 2017335497, First Examination Report dated Jun. 26, 2019", 3 pgs.

"Australian Application Serial No. 2017335497, Response filed Nov. 27, 2019 to First Examination Report dated Jun. 26, 2019", 18 pgs.

"European Application Serial No. 17762308.9, Response to Communication pursuant to Rules 161 & 162 filed Nov. 26, 2019", 23 pgs.

"International Application Serial No. PCT/US2017/048867, International Preliminary Report on Patentability dated Mar. 28, 2019", 8 pgs.

"International Application Serial No. PCT/US2017/048867, International Search Report dated Nov. 13, 2017", 5 pgs.

"International Application Serial No. PCT/US2017/048867, Written Opinion dated Nov. 13, 2017", 6 pgs.

(56) References Cited

OTHER PUBLICATIONS

"International Application Serial No. PCT/US2017/048896, International Preliminary Report on Patentability dated Apr. 11, 2019", 8 pgs.
"International Application Serial No. PCT/US2017/048896, International Search Report dated Nov. 27, 2017", 5 pgs.
"International Application Serial No. PCT/US2017/048896, Written Opinion dated Nov. 27, 2017", 6 pgs.
"International Application Serial No. PCT/US2017/052685, International Preliminary Report on Patentability dated Apr. 11, 2019", 6 pgs.
"International Application Serial No. PCT/US2017/052685, International Search Report dated Jan. 4, 2018", 5 pgs.
"International Application Serial No. PCT/US2017/052685, Written Opinion dated Jan. 4, 2018", 6 pgs.
"International Application Serial No. PCT/US2017/057367, International Preliminary Report on Patentability dated May 9, 2019", 6 pgs.
"International Application Serial No. PCT/US2017/057367, International Search Report dated Jan. 19, 2018", 4 pgs.
"International Application Serial No. PCT/US2017/057367, Written Opinion dated Jan. 19, 2018", 4 pgs.
"International Application Serial No. PCT/US2018/013257, International Preliminary Report on Patentability dated Jul. 25, 2019", 8 pgs.
"International Application Serial No. PCT/US2018/013257, International Search Report dated Apr. 19, 2018", 4 pgs.
"International Application Serial No. PCT/US2018/013257, Written Opinion dated Apr. 19, 2018", 6 pgs.
Ahern, David K., et al., "Comparison of lumbar paravertebral EMG patterns in chronic low back pain patients and non-patient controls", Pain, 34, (1988), 153-160.
Allum, John H.J., et al., "A speedy solution for balance and gait analysis: angular velocity measured at the centre of body mass", Current Opinion in Neurology 18, (2005), 15-21.
Alo, Kenneth M., et al., "Effect of Spinal Cord Stimulation on Sensory Nerve Conduction Threshold Functional Measures", Neuromodulation, vol. 3, No. 3, (2000), 145-154.
Ambady, Nalini, et al., "Thin Slices of Expressive Behavior as Predictors of Interpersonal Consequences: A Meta-Analysis", Psychological Bulletin, 1992, vol. 111, No. 2, 256-274.
Annoni, Elizabeth M., et al., "Method and Apparatus for Pain Management Using Objective Pain Measure", U.S. Appl. No. 62/400,336, filed Sep. 27, 2016.
Annoni, Elizabeth M., et al., "Pain Management Based on Brain Activity Monitoring", U.S. Appl. No. 62/445,061, filed Jan. 11, 2017.
Annoni, Elizabeth M., et al., "Pain Management Based on Muscle Tension Measurements", U.S. Appl. No. 62/445,092, filed Jan. 11, 2017.
Annoni, Elizabeth M., et al., "Pain Management Based on Respiration-Mediated Heart Rates", U.S. Appl. No. 62/445,069, filed Jan. 11, 2017.
Annoni, Elizabeth M., et al., "Patient-Specific Calibration of Pain Quantification", U.S. Appl. No. 62/445,095, filed Jan. 11, 2017.
Arsenault, Marianne, et al., "Pain Modulation Induced by Respiration: Phase and Frequency Effects", Neuroscience 252, (2013), 501-511.
Artner, Juraj, et al., "Prevalence of sleep deprivation in patients with chronic neck and back pain: a retrospective evaluation of 1016 patients", Journal of Pain Research: 6, (2013), 1-6.
Bakker, Jorn, et al., "What's your current stress level? Detection of stress patterns from GSR sensor data", Eindhoven University of Technology—The Netherlands, (2011), 1-8.
Baliki, Marwan N., et al., "Beyond Feeling: Chronic Pain hurts the Brain, Disrupting the Default-Mode Network Dynamics", The Journal of Neuroscience, 28 (6), (Feb. 6, 2008), 1398-1403.
Banos, Oresti, et al., "PhysioDroid: Combining Wearable Health Sensors and Mobile Devices for a Ubiquitous, Continuous, and Personal Monitoring", The Scientific World Journal, vol. 2014 Article ID 190824, (2014), 11 pgs.
Bansevicius, Dalius, et al., "Mental stress of long duration: EMG activity, perceived tension, fatigue, and pain development in pain-free subjects", Headache: The Journal of Head and Face Pain; 37.8, (1997), 499-510.
Barad, Meredith J., et al., "Complex Regional Pain Syndrome Is Associated With Structural Abnormalities in Pain-Related Regions of the Human Brain", The Journal of Pain, vol. 15. No. 2, (Feb. 2014), 197-203.
Barkley, Jacob E., et al., "The effect of spinal cord stimulation unit revision on perceived pain, anxiety, mobility and physical activity in individuals with low back/lower extremity pain", Kent State University—The Spine and Pain Institute, Presented at Annual Meeting of the North American Neuromodulation Society (NANS) on Dec. 11-14, 2014, 1 pg.
Bartlett, Marian Stewart, et al., "Automatic Decoding of Facial Movements Reveals Deceptive Pain Expressions", Current Biology 24, 738-743, Mar. 31, 2014.
Beneck, George J., et al., "Spectral analysis of EMG using intramuscular electrodes reveals non-linear fatigability characteristics in persons with chronic low back pain", Journal of Electromyography and Kinesiology 23, (2013), 70-77.
Ben-Israel, Nir, et al., "Monitoring the nociception level: a multi-parameter approach", J Clin Monit Comput 27, (2013), 659-668.
Berthomier, Christian, et al., "Automatic analysis of single-channel sleep EEG: validation in healthy individuals", Sleep-New York Then Westchester—30.11, (2007), 1587-1595.
Boselli, E., et al., "Prediction of immediate postoperative pain using the analgesia/nociception index: a prospective observational study", British Journal of Anaesthesia 112 (4):, (2014), 715-721.
Boselli, E., et al., "Prospective observational study of the non-invasive assessment of immediate postoperative pain using the analgesia/nociception index (ANI)", British Journal of Anaesthesia 111, (2013), 453-459.
Broucqsault-Dédrie, Celine, et al., "Measurement of Heart Rate Variability to Assess Pain in Sedated Critically Ill Patients: A Prospective Observational Study", PLOS One, (Jan. 25, 2016), 1-11.
Bunde, Armin, et al., "Correlated and uncorrelated regions in heart-rate fluctuations during sleep", Physical Review Letters 85.17, (2000), 3736-3739.
Chan, C. W.Y., et al., "Subjective pain sensation is linearly correlated with the Flexion reflex in man", Brain Research, 479, (1989), 145-150.
Chapman, C. Richard, et al., "Phasic pupil dilation response to noxious stimulation in normal volunteers: relationship to brain evoked potentials and pain report", (1999), 44-52.
Chen, Shuzhen, et al., "The role ofthe autonomic nervous system in hypertension: a bond graph model study", Physiological measurement 29.4 (2008): 473, (2008), 473-495.
Cheng, Qian, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), Sep. 25, 2013,, (2013), 1-10.
Chuang, Chiung-Cheng, et al., "Photoplethysmography variability as an alternative approach to obtain heart rate variability information in chronic pain patient", J Clin Monit Comput—Published online, (Feb. 24, 2015), 1-6.
Chung, Ok Y., "Baroreflex sensitivity associated hypoalgesia in healthy states is altered by chronic pain", Pain 138, (2008), 87-97.
Ciampi De Andrade, Daniel, et al., "Neurophysiological assessment of spinal cord stimulation in failed back surgery syndrome", Pain 150, (2010), 485-491.
Cinaz, Burcu, et al., "Monitoring of mental workload levels during an everyday life office-work scenario", Pers Ubiquit Comput 17, (2013), 229-239.
Clark, Bryan Allen, et al., "Pain Management Based on Functional Measurements", U.S. Appl. No. 62/445,075, filed Jan. 11, 2017.

(56) References Cited

OTHER PUBLICATIONS

Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.

Dansie, Elizabeth J., et al., "Activity in Adults with Chronic Widespread Pain", The Journal of Pain—Accepted Manuscript, (2014), 33 pgs.

Davydov, Dmitry M., et al., "Cardiovascular activity and chronic pain severity", Physiology & Behavior 152, 203-216 (2015).

De-La-Herran, Alvaro M., et al., "Gait Analysis Methods: An Overview of Wearable and Non-Wearable Systems, Highlighting Clinical Applications", Sensors 14, (2014), 3362-3394.

Denk, Franziska, et al., "Chronic Pain: Emerging Evidence for the Involvement of Epigenetics", Neuron 73 (3), (2012), 435-444.

Duschek, S., "Relationship between baroreceptor cardiac reflex sensitivity and pain experience in normotensive individuals", International Journal of Psychophysiology 65, (2007), 193-200.

Eisenberg, Elon, et al., "Quantitative Sensory Testing for Spinal Cord Stimulation in Patients With Chronic Neuropathic Pain", (2006), 161-165.

Elgendi, Mohamed, "On the analysis of fingertip photoplethysmogram signals", Current cardiology reviews 8.1, (2012), 14-25.

Evans, Subhadr, et al., "Heart rate variability as a biomarker for autonomic nervous system response differences between children with chronic pain and healthy control children", Journal of Pain Research 3.6, (2013), 449-457.

Fagius, J., et al., "The cold pressor test: effects on sympathetic nerve activity in human muscle and skin nerve fascicles", Acta physiologica Scandinavica 137.3, (1989), 325-334.

Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.

Foo, H., et al., "Brainstem modulation of pain during sleep and waking", Sleep medicine reviews 7.2, (2003), 145-154.

Frederiks, Joost, et al., "Within-subject electrocardiographic differences at equal heart rates: role of the autonomic nervous system", Pflügers Archiv 441.5, (2001), 717-724.

Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).

Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.

Gesche, Heiko, et al., "Continuous blood pressure measurement by using the pulse transit time: comparison to a cuff-based method", European journal of applied physiology 112.1, (2012), 309-315.

Godfrey, A., et al., "Direct measurement of human movement by accelerometry", Medical Engineering & Physics 30 (2008) 1364-1386.

Godfrey, A., et al., "Instrumenting gait with an accelerometer: a system and algorithm examination", Medical Engineering & Physics, Mar. 2015, doi:10.1016/j.medengphy.2015.02.003, 24 pgs.

Gouveia, S., et al., "Assessing Baroreflex Sensitivity in the Sequences Technique: Local versus Global Approach", Computers in Cardiology, 32, (2005), 279-282.

Granovsky, Yelena, et al., "Objective Correlate of Subjective Pain Perception by Contact Heat-Evoked Potentials", The Journal of Pain, vol. 9, No. 1, (Jan. 2008), 53-63.

Green, Alexande L., "Measurement of muscle sympathetic nerve activity reveals true sympathetic changes in chronic pain", Exp Physiol 97.10, (2012), 1083.

Hallman, David, et al., "Autonomic regulation, physical activity and perceived stress in subjects with musculoskeletal pain: 24-hour ambulatory monitoring", International Journal of Psychophysiology 86, (2012), 276-282.

Hallman, David M., et al., "Changes in physical activity and heart rate variability in chronic neck-shoulder pain: monitoring during work and leisure time", Int Arch Occup Environ Health 87, (2014), 735-744.

Hallman, David M., et al., "Long-Term Monitoring of Physical Behavior Reveals Different Cardiac Responses to Physical Activity among Subjects with and without Chronic Neck Pain", BioMed Research International, vol. 2015, Article ID 907432, 11 pages, http://dx.doi.org/10.1155/2015/907482, 11 pages.

Hartwich, Doreen, et al., "Effect of muscle metaboreflex activation on spontaneous cardiac baroreflex sensitivity during exercise in humans", J Physiol 589.24, (2011), 6157-6171.

Jensen, MP, et al., "Brain EEG activity correlates of chronic pain in persons with spinal cord injury: clinical implications", Nature; Spinal Cord; 51, (Jul. 17, 2012), 55-58.

Jess, Gunnar, et al., "Monitoring heart rate variability to assess experimentally induced pain using the analgesia nociception index—A randomised volunteer study", Eur J Anaesthesiol 32, (2015), 1-8.

Kang, Jon-Eun, et al., "Pulse transit time shows vascular changes caused by propofol in children", J Clin Monit Comput 29, (2015), 533-537.

Keefe, Francis J., et al., "An Objective Approach to Quantifing Pain Behavior and Gait Patterns in Low Back Pain Patients", Pain, 21, (1985), 153-161.

Kemler, Marius A., et al., "Impact of Spinal Cord Stimulation on Sensory Characteristics in Complex Regional Pain Syndrome Type 1—A Randomized Trial", Anesthesiology, 95, (2001), 72-80.

Keshari, Kayvan R., et al., "Lactic Acid and Proteoglycans as Metabolic Markers dor Discogenic Back Pain", Spine, vol. 13, No. 3, (2008), 312-317.

Kim, Young Uk, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.

Kodituwakku, Sandun, et al., "Point Process Respiratory Sinus Arrhythmia Analysis during Deep Tissue Pain Stimulation", Computing in Cardiology 38, (2011), 193-196.

Koenig, J., et al., "Heart rate variability and experimentally induced pain in healthy adults: A systematic review", European Journal of Pain 18, (2014), 301-314.

Koenig, Julian, et al., "Chronic Pain and Heart Rate Variability in a Cross-Sectional Occupational Sample Evidence for Impaired Vagal Control", The Clinical Journal of Pain, Publish Ahead of Print, (2015), 31 pgs.

La Rovere, Maria Teresa, et al., "Baroreflex Sensitivity: Measurement and Clinical Implications", Ann Noninvasive Electrodardiol, 13(2):191-207, 2008.

Lamoth, Claudine J.C., et al., "How do persons with chronic low back pain speed up and slow down? Trunk-pelvis coordination and erector spinae activity during gait", Gait & Posture 23, (2006), 230-239.

Lamoth, Claudine J.C., et al., "Peivis-Thorax Coordination in the Transverse Plane During Walking in Persons With Nonspecific Low Back Pain", Spine, vol. 27, No. 4, (2002), E92-E99.

Lane, James D., et al., "Respiratory Sinus Arrhythmia and Cardiovascular Responses to Stress", Psychophysiology, vol. 29, No. 4, (1992), 461-470.

Latremoliere, Alban, et al., "Reduction of Neuropathic and Inflammatory Pain through Inhibition of the Tetrahydrobiopterin Pathway", Neuron, 86 (6), (2015), 1393-1406.

Ledowski, Thomas, et al., "The influence of age and sex on the relationship between heart, rate variability, haemodynamic variables and subjective measures of acute post-operative pain", European Journal of Anaesthesiology, vol. 28, No. 6, (2011), 433-437.

Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.

Lidberg, Lars, et al., "Sympathetic Skin Nerve Dischai gcs in Relation lo Anipiiliule ol Skin Resistance Responses", Psychophysiology, vol. 18, No. 3, (May 1981), 268-270.

(56) References Cited

OTHER PUBLICATIONS

Littlewort, Gwen C., et al., "Automatic Coding of Facial Expressions Displayed During Posed and Genuine Pain", Image and Vision Computing, 27(12) p. 1741-1844.
Logier, R., et al., "PhysioDoloris: a monitoring device for Analgesia / Nociception balance evaluation using Heart Rate Variability analysis", 32nd Annual International Conference of the IEEE EMBS, (2010), 1194-1197.
Looney, David, et al., "The In-the-Ear Recording Concept", IEEE Pulse Nov./Dec. 2012, 32-42.
Marchi, Antonio, et al., "Pain Biomarkers", Clin Drug Invest. 29 Suppl 1, (2009), 41-46.
Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.
Mauer, C,, et al., "Quantitative sensory testing in the German Research Network on Neuropathic Pain (DFNS): Somatosensory abnormalities in 1236 patients with different neuropathic pain syndromes", Pain 150, (2010), 439-450.
McBeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.
McCarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.
McCracken, Lance M., et al., "Disrupted sleep patterns and daily functioning in patients with chronic pain", Pain Res Manage vol. 7 No. 2 Summer 2002 75-79.
Mikkelsen, Kaare B., et al., "EEGRecordedfromtheEar:CharacterizingtheEar-EEGMethod", FrontiersinNeuroscience|www.frontiersin.org, Nov. 2015|vol. 9|Article438, 8 pgs.
Mironer, Y. Eugene, et al., "Pain Tolerance Threshold: A Pilot Study of an Objective Measurement of Spinal Cord Stimulator Trial Results", Pain Medicine, vol. 1, No. 2, (2000), 110-115.
Moseley, G. Lorimer, et al., "Tactile Discrimination, but not tactile stimulation alone, reduces chronic limg pain", Pain 137, (2008), 600-608.
Moxham, I.M., "Understanding Arterial Pressure Waveforms", Southern African Journal of Anaesthesia and Analgesia 9.1, (2003), 40-42.
Mukkamala, R., et al., "Toward ubiquitous blood pressure monitoring via pulse transit time: theory and practice", IEEE Transactions on Biomedical Engineering 62.8, (2015), 1879-1901.
Mylius, Vett, et al., "Sex differences in nociceptive withdrawal reflex and pain perception", Somatosensory and Motor Research 22 (3), (Sep. 2005), 207-211.
Neblett, Randy, et al., "What Is The Best Surface EMG Measure of Lumbar Flexion-Relation for Distinguishing Chronic Low Back Pain Patients From Pain-Free Controls?", Clin J Pain 29 (4)—NIH Public Access, (Apr. 2013), 334-340.
Ng, Joseph, et al., "EMG activity of trunk muscles and torque output during isometric axial rotation exertion: a comparison between back pain patients and matched controls", Journal of Orthopaedic Research; 20, (2002), 112-121.
Palermo, Tonya M., et al., "Subjective Sleep Disturbances in Adolescents With Chronic Pain: Relationship to Daily Functioning and Quality of Life", The Journal of Pain, vol. 6, No. 3, (Mar. 2995), 201-207.
Panjabi, Manohar, "Clinical spinal instability and low back pain", Journal of Electromyography and Kinesiology 13, (2003), 371-379.
Patti, Gary J., et al., "Metabolomics implicates altered sphingolipids in chronic pain of neuropathic origin", nature chemical biology, vol. 8, (Mar. 2012), 232-234.
Perruchoud, Christophe, et al., "Assessment of Physical Activity of Patients with Chronic Pain", Neuromodulation: Technology at the Neural Interface; 17, (2012), 42-47.
Pinheiro, Eulália Silva Dos Santos, et al., "Electroencephalographic Patterns in Chronic Pain: A Systematic Review of the Literature", PLOS ONE | DOI:10.1371/journal.pone.0149085 Feb. 25, 2016, 27 pgs.
Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.
Pleger, Burkhard, et al., "Patterns of cortical reorginization parallel impaired tactile discrimination and pain intensity in complex regional pain syndrome", NeuroImage 32, (2006), 503-510.
Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.
Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.
Prichep, Leslie S., et al., "Evaluation of the Pain Matrix Using EEG Source Localization: A Feasibility Study", Pain Medicine 12, (2011), 1241-1248.
Prkachin, Kenneth, "The consistency of facial expressions of pain: a comparison across modalities", Pain, 51, (1992), 279-306.
Raminen, Tina, et al., "The Impact of Spinal Cord Stimulation on Sleep Patterns", Neuromodulation 19, (2016), 477-481.
Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.
Rhudy, Jamie L., et al., "Defining the nociceptive flexion reflex (NFR) threshold in human participants: A comparison of different scoring criteria", Pain 128, (2007), 244-253.
Roy, Sourav Dey, et al., "An Approach for Automatic Pain Detection through Facial Expression", Procedia Computer Science 84 (2016) 99-106.
Sacco, Marcella, et al., "The Relationship Between Blood Pressure and Pain", The Journal of Clinical Hypertension vol. 15, No. 8, (Aug. 2013), 600-605.
Sano, Akane, et al., "Quantitative analysis of wrist electrodermal activity during sleep", Int J Psychophysiol. Dec. 2014 ; 94(3), (2014), 382-389.
Sarnthein, Johannes, et al., "Increased EEG power and slowed dominant frequncy in patients with neurogenic pain", Brain 129, (2005), 55-64.
Sato, Karina L/, et al., "Spinal Cord Stimulation (SCS) Improves Decreased Physical Activity Induced by Nerve Injury", Behavioral Neuroscience, vol. 128, No. 5, (2914), 625-632.
Sawada, Yukihiro, et al., "Normalized pulse volume (NPV) derived photo-plethysmography as a more valid measure of the finger vascular tone", International Journal of Psychophysiology 41, (2001), 1-10.
Sayar, Kemal, et al., "Sleep Quality in Chronic Pain Patients", Can J. Psychiatry, vol. 47, No. 9, (Nov. 2002), 844-848.
Schulman, Joshua J., et al., "Thalamocortical dysrhythmia syndrome: MEG imaging of neuropathic pain", (Jul. 25, 2014), 33-39.
Schulz, Enrico, et al., "Prefrontal Gamma Oscillations Encode Tonic Pain in Humans", Cerebral Cortex 2015, (Mar. 8, 2015), 1-8.
Sesay, Musa, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.
Shouldice, R., "PR and PP ECG intervals as indicators of autonomic nervous innervation of the cardiac sinoatrial and atrioventricular nodes", Neural Engineering, 2003. Conference Proceedings. First International IEEE EMBS Conference on. IEEE, (Mar. 2003), 261-264.
Siddall, Phillip J., et al., "Magnetic Resonance Spectroscopy Detects Biochemical Changes in the Brain Associated with Chronic Low Back Pain: A Preliminary Report", Anesth Analg 102, (2006), 1164-1168.

(56) References Cited

OTHER PUBLICATIONS

Sihvonen, T., et al., "Electric behavior of low back muscles during lumbar pelvic rhythm in low back pain patients and healthy controls", Archives of physical medicine and rehabilitation; 72.13, (1991), 1080-1087.
Simoes, Mario A., "Feasibility of Wearable Sensors to Determine Gait Parameters", University of South Florida Scholar Commons, (2011), 1-98.
Skljarevski, V., et al., "The nociceptive flexion reflex in humans—review article", Pain, 96, (2002), 3-8.
Smallwood, Rachel F., et al., "Structural Brain Anomalies and Chronic Pain: A Quantitative Meta-Anaiysis of Gray Matter Volume", The Journal of Pain, vol. 14, No. 7, (Jul. 2013), 663-675.
Srivastava, Kyle Harish, et al., "Pain Management Based on Cardiovascular Parameters", U.S. Appl. No. 62/445,053, filed Jan. 11, 2017.
Srivastava, Kyle Harish, et al., "Pain Management Based on Emotional Expression Measurements", U.S. Appl. No. 62/445,082, filed Jan. 11, 2017.
Staud, Roland, "Heart rate variability as a biomarker of fibromyalgia syndrome", Fut Rheumatol 3 (5)—NIH Public Access, (Oct. 1, 2008), 475-483.
Storm, H., et al., "Skin conductance correlates with perioperative stress", Acta Anaesthesiol Scand 46, (2002), 887-895.
Sturgeon, John A., et al., "Respiratory Sinus Arrhythmia: a Marker of Resilience to Pain Induction", Int.J. Behav. Med. 21, (2014), 961-965.
Swenne, C. A., "Baroreflex sensitivity: mechanisms and measurement", Neth Heart J 21, (2013), 58-60.
Symons, Frank J., et al., "Can Biomarkers Differentiate Pain and No Pain Subgroups of Nonverbal Children with Cerebral Palsy? A Preliminary Investigation Based on Noninvasive Saliva Sampling", Pain Med 16 (2), (2015), 249-256.
Tagliazucchi, Enzo, et al., "Brain resting state is disrupted in chronic back pain patients", Neurosci Lett. 485 (1)—NIH Public Access, (Nov. 12, 2010), 26-31.
Tao, Weijun, et al., "Gait Analysis Using Wearable Sensors", Sensors 12, (2012), 2255-2283.
Tauda, Makoto, et al., "P2X4receptorsandneuropathicpain", Frontiers in Cellular Neuroscience, vol. 7, Article 191, (Oct. 28, 2013), 1-6.
Terkelsen, Astrid J., et al., "Heart Rate Variability in Complex Regional Pain Syndrome during Restand Mental and Orthostatic Stress", Anesthesiology, vol. 116, No. 1, (Jan. 2012), 133-146.
Thakur, Pramodsingh Hirasingh, et al., "Method and Apparatus for Pain Control Using Baroreflex Sensitivity During Posture Change", U.S. Appl. No. 62/412,587, filed Oct. 25, 2016.
Thakur, Pramodsingh Hirasingh, et al., "Systems and Methods for Closed-Loop Pain Management", U.S. Appl. No. 62/400,313, filed Sep. 27, 2016.
Thankur, Pramodsingh Hirasingh, et al., "Method and Apparatus for Pain Management Using Heart Sounds", U.S. Appl. No. 62/395,641, filed Sep. 16, 2016.
Theuvenel, Peter J., et al., "Responses to Median and Tbial Nerve Stimulation in Patients with Chronic Neuropathic Pain", Brain Topography, vol. 11, No. 4, (1999), 306-313.
Uceyler, Nuncan, et al., "Differential expression of cytokines in painful and painless neuropathies", (2007).
Uzar, E., et al., "Serum cytokine and pro-brain natriuretic peptide (BNP) levels in patients with migraine", European Review for Medical and Pharmacological Sciences; 15, (2011), 1111-1116.
Van Velzen, Marit H.N., et al., "Effect of heat-induced pain stimuli on pulse transit time and pulse wave amplitude in healthy volunteers", Physiological Measurement 37. (2016), 52-66.
Villarejo, Viqueira Maria, et al. "A Stress Sensor Based on Galvanic Skin Response (GSR) Controlled by ZigBee", Sensors 12, (2012), 6075-6101.
Walton, K. D., et al., "Abnormal thalamocortical activity in patients with Complex Regional Pain Syndrome (CRPS) Type 1", Pain 150, (2010), 41-51.

Willer, Jean Claude, "Comparative Study of Perceived Pain and Nociceptive Flexion Reflex in Man", Pain, 3, (1977), 69-80.
Williams, Dewayne P., et al., "Effects of Chronic Pelvic Pain on Heart Rate Variability in Women", The Journal of Urology, vol. 194,, (Nov. 2015), 1-6.
Wong, Arnold Y.L., et al., "Does experimental low back pain change posteroanterior lumbar spinal stiffness and trunk muscle activity? A randomized crossover study", Clinical Biomechanics 34, (2016), 45-52.
Wong, Jih-Sen, et al., "A comparative study of pulse rate variability and heart rate variability in healthy subjects", J Clin Monit Comput 26, (2012), 107-114.
Wu, Hao-Yu, et al., "Eulerian Video Magnification for Revealing Subtle Changes in the World", ACM Transactions on Graphics 31(4), (2012), 1-8.
Zamuner, Antonio R., et al., "Respiratory Sinus Arrhythmia and its Association with Pain in Women with Fibromyalgia Syndrome", Pain Practice, vol. 16, Issue 6, (2016), 704-711.
Zamunér, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.
Zeng, Zhihong, et al., "A Survey of Affect Recognition Methods: Audio, Visual and Spontaneous Expressions", ICMI'07, Nov. 12-15, 2007, 126-133.
Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.
Zhou, Jing, et al., "Recurrent Convolutional Neural Network Regression for Continuous Pain Intensity Estimation in Video", arXiv preprint arXiv:1605.00894 (2016) 84-92.
Zhou, Jing, et al., "Recurrent Convolutional Neural Network Regression for Continuous Pain Intensity Estimation in Video", Technical Report, (May 3, 2016), 1-11.
"U.S. Appl. No. 15/788,403, 312 Amendment filed Apr. 22, 2020", 8 pgs.
"U.S. Appl. No. 15/788,403, Corrected Notice of Allowability dated Mar. 18, 2020", 2 pgs.
"U.S. Appl. No. 15/788,403, Notice of Allowance dated Jan. 23, 2020", 7 pgs.
"U.S. Appl. No. 15/788,403, PTO Response to Rule 312 Communication dated Apr. 30, 2020", 2 pgs.
"U.S. Appl. No. 15/867,767, Notice of Allowance dated Apr. 6, 2020", 5 pgs.
"U.S. Appl. No. 15/867,767, Response filed Mar. 4, 2020 to Non Final Office Action dated Dec. 17, 2019", 10 pgs.
"U.S. Appl. No. 15/867,772, Non Final Office Action dated Apr. 2, 2020", 9 pgs.
"U.S. Appl. No. 15/867,789, Non Final Office Action dated Apr. 2, 2020", 10 pgs.
"U.S. Appl. No. 15/867,801, Notice of Allowance dated Feb. 5, 2020", 8 pgs.
"U.S. Appl. No. 15/867,873, Non Final Office Action dated Apr. 3, 2020", 11 pgs.
"U.S. Appl. No. 15/867,873, Notice of Allowance dated Oct. 22, 2020", 5 pgs.
"U.S. Appl. No. 15/867,873, Response filed Jun. 30, 2020 to Non Final Office Action dated Apr. 1, 2020", 10 pgs.
"U.S. Appl. No. 15/888,808, Advisory Action dated Feb. 10, 2020", 2 pgs.
"U.S. Appl. No. 15/888,808, Examiner Interview Summary dated Aug. 3, 2020", 3 pgs.
"U.S. Appl. No. 15/888,808, Non Final Office Action dated Jul. 2, 2020", 11 pgs.
"U.S. Appl. No. 15/888,808, Notice of Allowance dated Nov. 30, 2020", 9 pgs.
"U.S. Appl. No. 15/888,808, Response filed Jan. 31, 2020 to Final Office Action dated Dec. 16, 2019", 11 pgs.
"U.S. Appl. No. 15/888,808, Response filed Mar. 16, 2020 to Advisory Action dated Feb. 10, 2020", 8 pgs.
"U.S. Appl. No. 15/888,808, Response filed Sep. 29, 2020 to Non Final Office Action dated Jul. 2, 2020", 11 pgs.

(56) References Cited

OTHER PUBLICATIONS

"U.S. Appl. No. 16/034,304, Examiner Interview Summary dated Sep. 15, 2020", 3 pgs.
"U.S. Appl. No. 16/034,304, Final Office Action dated Jul. 27, 2020", 11 pgs.
"U.S. Appl. No. 16/034,304, Non Final Office Action dated Apr. 3, 2020", 15 pgs.
"U.S. Appl. No. 16/034,304, Notice of Allowance dated Sep. 29, 2020", 8 pgs.
"U.S. Appl. No. 16/034,304, Response filed Jun. 30, 2020 to Non Final Office Action dated Apr. 3, 2020", 13 pgs.
"U.S. Appl. No. 16/034,304, Response filed Sep. 16, 2020 to Final Office Action dated Jul. 27, 2020", 11 pgs.
"U.S. Appl. No. 16/800,822, Non Final Office Action dated Nov. 29, 2021", 5 pgs.
"U.S. Appl. No. 16/800,822, Notice of Allowance dated May 18, 2022", 7 pgs.
"U.S. Appl. No. 16/800,822, Response filed Feb. 3, 2022 to Non Final Office Action dated Nov. 29, 2021", 7 pgs.
"U.S. Appl. No. 16/820,474, Corrected Notice of Allowability dated Feb. 9, 2022", 2 pgs.
"U.S. Appl. No. 16/820,474, Non Final Office Action dated Oct. 12, 2021", 7 pgs.
"U.S. Appl. No. 16/820,474, Notice of Allowance dated Jan. 25, 2022", 7 pgs.
"U.S. Appl. No. 16/820,474, Response filed Dec. 16, 2021 to Non Final Office Action dated Oct. 12, 2021", 9 pgs.
"U.S. Appl. No. 16/821,161, Non Final Office Action dated Jan. 3, 2022", 5 pgs.
"U.S. Appl. No. 16/821,161, Notice of Allowance dated Apr. 4, 2022", 7 pgs.
"U.S. Appl. No. 16/821,161, Response filed Jan. 27, 2022 to Non Final Office Action dated Jan. 3, 2022", 8 pgs.
"U.S. Appl. No. 16/848,580, Examiner Interview Summary dated Feb. 4, 2022", 3 pgs.
"U.S. Appl. No. 16/848,580, Examiner Interview Summary dated Jun. 29, 2022", 2 pgs.
"U.S. Appl. No. 16/848,580, Final Office Action dated May 10, 2022", 17 pgs.
"U.S. Appl. No. 16/848,580, Non Final Office Action dated Jan. 4, 2022", 14 pgs.
"U.S. Appl. No. 16/848,580, Notice of Allowance dated Aug. 31, 2022", 8 pgs.
"U.S. Appl. No. 16/848,580, Response filed Feb. 2, 2022 to Non Final Office Action dated Jan. 4, 2022", 11 pgs.
"U.S. Appl. No. 16/848,580, Response filed Jun. 27, 2022 to Final Office Action dated May 10, 2022", 12 pgs.
"U.S. Appl. No. 17/095,642, Non Final Office Action dated Feb. 17, 2022", 13 pgs.
"U.S. Appl. No. 17/095,642, Notice of Allowance dated May 4, 2022", 8 pgs.
"U.S. Appl. No. 17/095,642, Response filed Mar. 31, 2022 to Non Final Office Action dated Feb. 17, 2022", 9 pgs.
"U.S. Appl. No. 17/145,514, Examiner Interview Summary dated Sep. 14, 2022", 2 pgs.
"U.S. Appl. No. 17/145,514, Non Final Office Action dated Aug. 4, 2022", 7 pgs.
"U.S. Appl. No. 17/145,514, Notice of Allowance dated Oct. 5, 2022", 5 pgs.
"U.S. Appl. No. 17/145,514, Response filed Sep. 26, 2022 to Non Final Office Action dated Aug. 4, 2022", 8 pgs.
"U.S. Appl. No. 17/188,300, Examiner Interview Summary dated Dec. 14, 2022", 2 pgs.
"U.S. Appl. No. 17/188,300, Non Final Office Action dated Sep. 22, 2022", 15 pgs.
"U.S. Appl. No. 17/188,300, Response filed Dec. 21, 2022 to Non Final Office Action dated Sep. 22, 2022", 12 pgs.
"Australian Application Serial No. 2017334841, Response filed Feb. 6, 2020 to First Examination Report dated Jun. 24, 2019", 14 pgs.
"European Application Serial No. 17778108.5, Response to Communication Pursuant to Rules 161 and 162 filed Dec. 2, 2019", 3 pgs.
"European Application Serial No. 17794503.7, Communication Pursuant to Article 94(3) EPC dated Nov. 7, 2022", 3 pgs.
"European Application Serial No. 17794503.7, Response to Communication Pursuant to Rules 161 and 162 filed Dec. 30, 2019", 11 pgs.
"European Application Serial No. 18701908.8, Communication Pursuant to Article 94(3) EPC dated May 20, 20", 6 pgs.
"European Application Serial No. 18701908.8, Response filed Sep. 29, 2020 to Communication Pursuant to Article 94(3) EPC dated May 20, 2020", 29 pgs.
"European Application Serial No. 18701908.8, Response to Communication Pursuant to Rules 161 and 162 filed Mar. 16, 2020", 8 pgs.
"European Application Serial No. 18702012.8, Response to Communication Pursuant to Rules 161 and 162 filed Mar. 11, 2020", 12 pgs.
"European Application Serial No. 18704105.8, Response to Communication Pursuant to Rules 161 and 162 filed Feb. 27, 2020", 10 pgs.
"European Application Serial No. 21188652.8, Extended European Search Report dated Nov. 24, 2021", 9 pgs.
"European Application Serial No. 21188652.8, Response filed Jul. 4, 2022 to Extended European Search Report dated Nov. 24, 2021", 10 pgs.
"International Application Serial No. PCT/US2018/013251, International Preliminary Report on Patentability dated Jul. 25, 2019", 7 pgs.
"International Application Serial No. PCT/US2018/013251, International Search Report dated Apr. 12, 2018", 4 pgs.
"International Application Serial No. PCT/US2018/013251, Written Opinion dated Apr. 12, 2018", 5 pgs.
"International Application Serial No. PCT/US2018/013268, International Preliminary Report on Patentability dated Jul. 25, 2019", 13 pgs.
"International Application Serial No. PCT/US2018/013268, International Search Report dated Apr. 30, 2018", 5 pgs.
"International Application Serial No. PCT/US2018/013268, Written Opinion dated Apr. 30, 2018", 11 pgs.
"International Application Serial No. PCT/US2018/041860, International Preliminary Report on Patentability dated Jan. 30, 2020", 7 pgs.
"International Application Serial No. PCT/US2018/041860, International Search Report dated Oct. 17, 2018", 4 pgs.
"International Application Serial No. PCT/US2018/041860, Written Opinion dated Oct. 17, 2018", 5 pgs.
Ashraf, A B, et al., "The painful face—Pain expression recognition using active appearance models", Image and Vision Computing Elsevier Guildford, GB, vol. 27, No. 12, (Nov. 1, 2009), 1788-1796.
Sotocinal, S G, et al., "The Rat Grimace Scale partially automated method for quantifying pain in the laboratory rat via facial expressions", Molecular Pain Biomed Central, London, GB, vol. 7 No. 1, (Jul. 29, 2011), 1744-8069.

US 11,751,804 B2

METHOD AND APPARATUS FOR PAIN MANAGEMENT USING OBJECTIVE PAIN MEASURE

CLAIM OF PRIORITY

This application is a continuation of U.S. application Ser. No. 15/688,676, filed Aug. 28, 2017, which claims the benefit of priority under 35 U.S.C. § 119(e) of U.S. Provisional Patent Application Ser. No. 62/400,336, filed on Sep. 27, 2016, each of which is herein incorporated by reference in their entirety.

CROSS REFERENCE TO RELATED APPLICATIONS

This application is related to commonly assigned U.S. Provisional Patent Application Ser. No. 62/400,313, entitled "SYSTEMS AND METHODS FOR CLOSED-LOOP PAIN MANAGEMENT", filed on Sep. 27, 2016 and U.S. Provisional Patent Application Ser. No. 62/395,641, entitled "METHOD AND APPARATUS FOR PAIN MANAGEMENT USING HEART SOUNDS", filed on Sep. 16, 2016, which are incorporated by reference in their entirety.

TECHNICAL FIELD

This document relates generally to medical devices and more particularly to a pain management system that uses sensed physiological and/or functional parameters to produce an objective measure for pain.

BACKGROUND

Pain may result from an injury, a disease (e.g., arthritis, fibromyalgia), or even a medical treatment (e.g., certain cancer treatment). Various treatments are applied for pain management, such as medication, psychotherapy, electrical stimulation, thermal therapy, and their various combinations. Examples of electrical stimulation for pain management include Transcutaneous Electrical Nerve Stimulation (TENS) delivered by a TENS unit and Spinal Cord Stimulation (SCS) that may be delivered by an implantable neuromodulation systems. Pain treatment may be prescribed based on an assessment of a patient's symptoms and underlying conditioning and titrated based on the patient's response to the treatment. As pain is not directly measurable by a machine, the assessment of the condition and the titration of the therapy may depend on questioning the patient.

SUMMARY

An example (e.g., "Example 1") of a system for managing pain of a patient may include a pain monitoring circuit, a pain relief device, and a control circuit. The pain monitoring circuit may include a parameter analyzer and a pain score generator. The parameter analyzer may be configured to receive and analyze at least two parameters selected from a physiological parameter indicative of a physiological function or state of the patient, a functional parameter indicative of a physical activity or state of the patient, or a patient parameter including subjective information provided by the patient. The pain score generator may be configured to compute a composite pain score using an outcome of the analysis. The composite pain score may indicate a degree of the pain. The pain relief device may be configured to deliver one or more pain-relief therapies. The control circuit may be configured to control the delivery of the one or more pain-relief therapies using the composite pain score and therapy parameters.

In Example 2, the subject matter of Example 1 may optionally be configured such that the parameter analyzer is configured to produce a signal metric using the at least two parameters, and the pain score generator is configured to compute the composite pain score using the signal metric.

In Example 3, the subject matter of Example 2 may optionally be configured such that the parameter analyzer is configured to generate one or more weighting factors and is configured to produce the signal metric using the at least two parameters with the one or more weighting factors each applied to a parameter of the at least two parameters.

In Example 4, the subject matter of Example 3 may optionally be configured such that the parameter analyzer is configured to adjust the one or more weighting factors by automatic adaptation to the patient over time.

In Example 5, the subject matter of any one or any combination of Examples 1 to 4 may optionally be configured such that the pain monitoring circuit further include: one or more physiological signal sensors configured to sense one or more physiological signals from the patient, a physiological signal sensing circuit configured to process the one or more physiological signals, a physiological parameter generator configured to generate the physiological parameter using the processed one or more physiological signals, one or more functional signal sensors to sense one or more functional signals from the patient, a functional signal sensing circuit configured to process the one or more functional signals, and a functional parameter generator configured to generate the functional parameter using the processed one or more functional signals.

In Example 6, the subject matter of Example 5 may optionally be configured such that the one or more physiological signal sensors include a sensor configured to sense a physiological signal indicative of change in sympathetic activity, and the physiological parameter generator is configured to generate a physiological parameter being a measure of the change in sympathetic activity.

In Example 7, the subject matter of Example 5 may optionally be configured such that the one or more physiological signal sensors include a sensor configured to sense a physiological signal indicative of a neural activity, and the physiological parameter generator is configured to generate a physiological parameter being a measure of the neural activity.

In Example 8, the subject matter of Example 5 may optionally be configured such that the one or more functional signal sensors include a sensor configured to sense a function signal indicative of a measure of movement or posture, and the functional parameter generator is configured to generate a functional parameter quantitatively indicative the measure of movement or posture.

In Example 9, the subject matter of any one or any combination of Examples 1 to 8 may optionally be configured to include a patient information input device configured to receive patient information related to pain, a patient information processing circuit configured to process the patient information, and a patient parameter generator configured to generate the patient parameter using the processed patient information.

In Example 10, the subject matter of any one or any combination of Examples 1 to 9 may optionally be configured such that the pain relief device includes a neuromodulator to deliver a neuromodulation therapy including electrical stimulation.

In Example 11, the subject matter of any one or any combination of Examples 1 to 10 may optionally be configured such that the pain relief device includes a drug pump.

In Example 12, the subject matter of any one or any combination of Examples 1 to 11 may optionally be configured to include an implantable medical device including the pain monitoring circuit, the pain relief device, and the control circuit, and the control circuit includes an implant control circuit.

In Example 13, the subject matter of Example 12 may optionally be configured to include an external device configured to be communicatively coupled to the implantable medical device. The external device includes the patient information input device including a patent input device configured to receive a parameter representative of intensity of the pain specified by the patient.

In Example 14, the subject matter of Example 13 may optionally be configured such that the external device is configured to receive the composite pain score, to produce a notification using the composite pain score, to determine one or more recipients of the notification using the composite pain score, and to control delivery of the notification to each of the one or more recipients.

In Example 15, the subject matter of Example 14 may optionally be configured such that the external device is configured to produce external commands for adjusting the therapy parameters using the composite pain score and the patient information and transmit the external commands to the implantable medical device, and the implant control circuit is configured to adjust the therapy parameters using the external commands.

An example (e.g., "Example 16") of a method for managing pain of a patient is also provided. The method may include receiving and analyzing at least two parameter selected from a physiological parameter indicative of a physiological function or state of the patient, a functional parameter indicative of a physical activity or state of the patient, and a patient parameter related to the pain automatically using a processor, the patient parameter including subjective information provided by the patient, computing a composite pain score using the processor based on an outcome of the analysis, the composite pain score indicating of a degree of the pain, delivering one or more pain-relief therapies using a pain relief therapy device, and controlling the delivery of the one or more pain-relief therapies from the pain relief therapy device automatically using the processor based on the composite pain score and therapy parameters.

In Example 17, the subject matter of Example 16 may optionally further include generating one or more weighting factors, and the subject matter of analyzing the at least two parameters as found in Example 16 may optionally include generating a signal metric using the at least two parameters with the one or more weighting factors each applied to a parameter of the at least two parameters, and the subject matter of computing the composite pain score as found in Example 16 may optionally include computing the composite pain score using the signal metric.

In Example 18, the subject matter of Example 17 may optionally further include adjusting the one or more weighting factors by automatic adaptation to the patient over time.

In Example 19, the subject matter of any one or any combination of Example 16 may optionally further include sensing one or more physiological signals from the patient using one or more physiological signal sensors, generating the physiological parameter based the one or more physiological signals using the processor, sensing one or more functional signals from the patient using one or more functional signal sensors, generating the functional parameter based the one or more functional signals using the processor, and receiving a parameter representative of intensity of the pain from the patient.

In Example 20, the subject matter of generating the physiological parameter as found in Example 19 may optionally include generating a measure of the change in sympathetic activity.

In Example 21, the subject matter of generating the physiological parameter as found in any one or any combination of Examples 19 and 20 may optionally include generating a measure of the neural activity.

In Example 22, the subject matter of generating the functional parameter as found in any one or any combination of Examples 19 to 21 may optionally include generating a functional parameter quantitatively indicative of a measure of movement or posture.

In Example 23, the subject matter of any one or any combination of Examples 16 to 22 may optionally include producing a notification using the composite pain score, determining one or more recipients of the notification using the composite pain score and one or more specified thresholds, and delivering the notification to each of the one or more recipients.

In Example 24, the subject matter of delivering the one or more pain-relief therapies using the pain relief therapy device as found in any one or any combination of Examples 16 to 23 may optionally include delivering one or more of a neuromodulation therapy including electrical stimulation or a drug therapy from an implantable medical device.

In Example 25, the subject matter of Example 24 may optionally further include adjusting the therapy parameters using the composite pain score and a patient command entered by the patient using an external device communicatively coupled to the implantable medical device.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
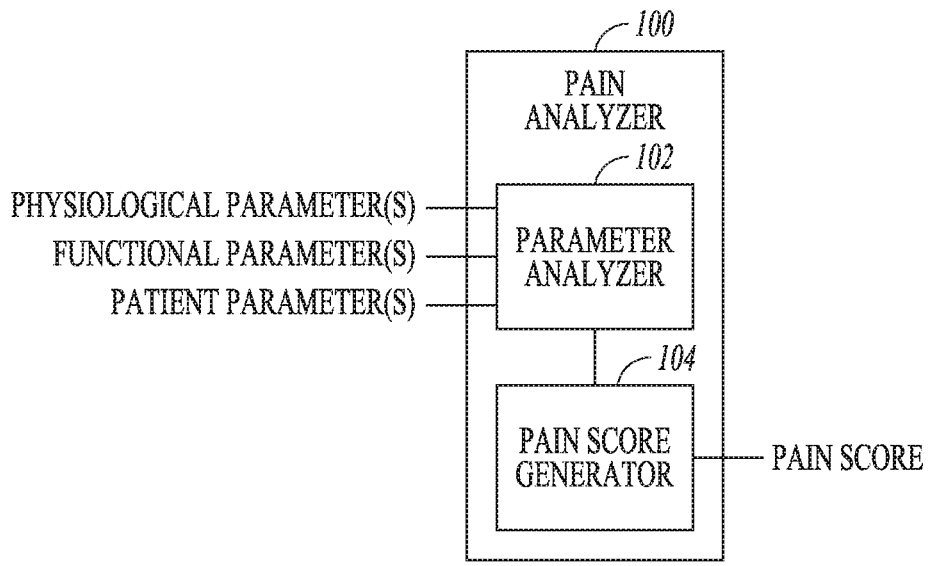
FIG. 1 illustrates an embodiment of a pain analyzer.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a pain management system that provides a quantitative measure of a patient's pain (or pain-related condition or symptom) for diagnostic, monitoring, and/or therapeutic purposes. The International Association for the Study of Pain (IASP, Washington, D.C., U.S.A.) defines pain as an "unpleasant sensory and emotional experience that is associated with the actual or potential tissue damage or described in such terms." While also experienced by healthy people, elevated levels of pain are experienced by many patients suffering from various types of injuries and diseases. Managing pain is a top priority of physicians and nurses. In a clinic, pain is often quantified by questioning the patient using the visual analog scale (VAS) or numeric rating scale (NRS). VAS allows the patient to indicate a point representing the perceived pain level in a continuum from no pain to the worst imaginable pain. NRS allows to patient to select a number between 0 and 10 representing the perceived pain level from no pain ("0") to the worst imaginable pain ("10"). However, the pain value as indicated by the patient is a subjective measure. One patient's "10" could be another patient's "1". In addition, monitoring and quantifying chronic pain presents additional challenges as the patient's perception of pain can change over time. Furthermore, some patients such as infants and disabled may have a challenge communicating their perception of pain. A lack of an objective measure of pain results in many challenges in healthcare besides such examples.

The subjective pain value can lead to challenges such as over and under dosing of analgesics (especially opioids), misdiagnosis, suboptimal therapy, extended hospital stay, and increased healthcare cost. Patients and their care providers can both benefit from a more objective measure of pain. Many measureable parameters are known to relate to pain (see Table 1). Such parameters, individually or in combination, may be measured in the present pain management system discussed in this document. In various embodiments, one or more of such parameters can be acquired to produce a pain score being a quantitative measure of pain. In various embodiments, this pain score can be used to adjust or optimize a pain relief therapy in a closed-loop pain management system. For example, a pain monitoring system producing such a pain score can be integrated into a closed-loop pain management system to titrate a pain control therapy. Examples of such pain control therapy can include any one or any combination of spinal cord stimulation (SCS), dorsal root ganglia (DRG) stimulation, deep brain stimulation (DBS), motor cortex stimulation (MCS), transcranial direct current stimulation (tDCS), transcutaneous spinal direct current stimulation (tsDCS), trigeminal nerve stimulation, occipital nerve stimulation, vagus nerve stimulation (VNS), sacral nerve stimulation, pudendal nerve stimulation, sphenopalatine ganglion stimulation, sympathetic nerve modulation, multifidus muscle stimulation, adrenal gland modulation, carotid baroreceptor stimulation, transcutaneous electrical nerve stimulation (TENS), transcranial magnetic stimulation (TMS), tibial nerve stimulation, transcranial magnetic stimulation (TMS), radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, other peripheral tissue denervation therapies, drug therapy (such as delivered from a drug pump), and nerve blocks or injections (such as pharmaceuticals or biologics).

Pain alters various physiological and functional signals that can be sensed from the patient invasively or non-invasively. Such signals can be used to quantify the patient's pain levels. Physiological signals such as heart rate, blood pressure, respiration rate, and skin conductance, as well as signals derived from these such as heart rate variability, may show abnormal patterns when the patient experiences pain, due to the patient's sympathetic activity elevated by pain. The physiological signals indicative of level of sympathetic activity can therefore be collected via invasive and/or non-invasive means for analysis of the patient pain state. Pain is felt by the patient through transmission of neural signals in the patient's nervous system. Thus, pain can be measured more directly by sensing the patient's neural activities. Pain alters neuronal connection, resulting in predictable changes in electrical activity in the nervous system that can be captured by, for example, electroencephalography (EEG) and electromyography (EMG), which can be analyzed to assess the patient's pain by evaluating neural function. Functional signals such as those indicative of a measure of movement (e.g., activity level, gait pattern, range of motion, or sleep) or posture can also indicate the patient's pain state, because pain can impact various functional aspects of the patient's daily activities when the patient has to compensate for discomfort during the activities. For example, the patient may try to reduce pain with irregular gait patterns and/or lower activity levels. Such functional signals can also be monitored for analyzing the patient pain state. In various embodiments, such physiological and functional parameters when used individually or in various combinations can provide for an objective and quantitative measure of the patient's pain.

In addition to the physiological and/or functional parameters, the analysis of pain can also include subjective input from the patient. For example, the patient's mood and mental state such as stress level and sleep quality can impact the patient's perception of pain. Furthermore, the analysis of pain can also include environmental parameters such as temperature, humidity, and/or air pressure, which may influence discernment of pain. Time of day, which may capture circadian influence on pain, can also be included in the analysis of pain.

In various embodiments, the present pain management system can sense pain-indicating physiological and functional signals and analyze the signals using an objective method to produce a quantitative measure representative of the pain state of the patient, to control therapy delivery, and to evaluate efficacy of therapeutic intervention for pain. In various embodiments, outcomes of the analysis can include an objective pain measure based on one or more physiological parameters and one or more function parameter. In various embodiments, the objective pain measure is further combined with relevant medical history of the patient and/or input received from the patient or their caregivers to produce a composite pain score. This pain score represents the patient's pain intensity and can be reported to the patient and/or a care provider, and can be used to start, stop, and adjust pain management therapies.

While various physiological or functional parameters have been studied for indicating or measuring pain, the present pain management system combines both physiological and functional parameters to better capture the patient's pain experience and quantify the pain experience into an objective pain value (e.g., the composite pain score). For example, the system can include sensors for sensing the physiological and functional signals, a patient information input to receive patient information such as subjective pain level perceived by the patient and/or pain-related information in the patient's medical history, a processing circuit to produce the physiological and functional parameters by extracting relevant information from the sensed signals and computing the composite pain score based on the physiological and functional parameters and the patient information. The composite pain score as well as the algorithm for its computation can be updated continuously, periodically, according to other schedules, or as needed to reflect the changes in the physiological and functional parameters and the patient information. The composite pain score can be used for monitoring the patient's pain state and/or titrating one or more pain relief therapies the patient receives.

FIG. 1 illustrates an embodiment of a pain analyzer 100 that can include a parameter analyzer 102 and a pain score generator 104. In the illustrated embodiment, parameter analyzer 102 receives and analyzes one or more physiological parameters each indicative of a physiological function or state of a patient, one or more functional parameters each indicative of a physical activity or state of the patient, and one or more patient parameters related to the pain, such as a parameter representative of intensity of the pain specified by the patient. Pain score generator 104 computes a composite pain score using an outcome of the analysis. The composite pain score indicates a degree of the pain. In various embodiments, parameter analyzer 102 can receive and analyze at least one physiological parameter and one functional parameter. Pain score generator 104 can compute a composite pain score using an outcome of the analysis.

In various embodiments, parameter analyzer 102 can produce a signal metric using one or more physiological parameters, one or more functional parameters, and/or the one or more patient parameters. In one embodiment, parameter analyzer 102 produces the signal metric using at least one parameter selected from the one or more physiological parameters, the one or more functional parameters, or the one or more patient parameters. In one embodiment, parameter analyzer 102 produces the signal metric using at least two parameters selected from the one or more physiological parameters, the one or more functional parameters, or the one or more patient parameters. In one embodiment, parameter analyzer 102 produces the signal metric using at least one physiological parameter and one functional parameter. In one embodiment, parameter analyzer 102 produces the signal metric using at least two parameters selected from a physiological parameter, a functional parameter, and a patient parameter. In one embodiment, parameter analyzer 102 produces the signal metric using the one or more physiological parameters and the one or more functional parameters. In one embodiment, parameter analyzer 102 produces the signal metric using the one or more physiological parameters and the one or more patient parameters. In one embodiment, parameter analyzer 102 produces the signal metric using the one or more functional parameters and the one or more patient parameters. In one embodiment, parameter analyzer 102 produces the signal metric using the one or more physiological parameters, the one or more functional parameters, and the one or more patient parameters.

The signal metric can be a linear or nonlinear combination of the one or more physiological parameters, the one or more functional parameters, and/or the one or more patient parameters. In various embodiments, parameter analyzer 102 can produce the signal metric using the one or more physiological parameters, the one or more functional parameters, and/or the one or more patient parameters with the weighting factors each applied to one of these parameters. In various embodiments, parameter analyzer 102 can adjust the weighting factors through automatic learning and adaptation to the patient over time (e.g., based on stored parameters and/or outcomes of analysis, such as features extracted from the parameters). In various other embodiments, parameter analyzer 102 can allow the weighting factors to be adjusted manually. In various other embodiments, the weighting factors can be adjusted according to a calibration schedule or as needed, and the adjustment can be performed by a user such as a physician or other authorized care provider in a clinic, or initiated by the patient and performed by parameter analyzer 102 automatically at home. In various embodiments, the weighting factors can be patient-specific and dynamically changed based on the patient's conditions and/or activities, such as source of pain, type of pain, related pathological condition, physical condition (e.g., bed-ridden), time of day, and/or physical activity (e.g., patient being sleeping or walking).

In various embodiments, pain score generator 104 can compute the composite pain score using the signal metric. In one embodiment, pain score generator 104 trends the signal metric and computes the composite pain score based on the resulting trending of the signal metric.

Figure 2:
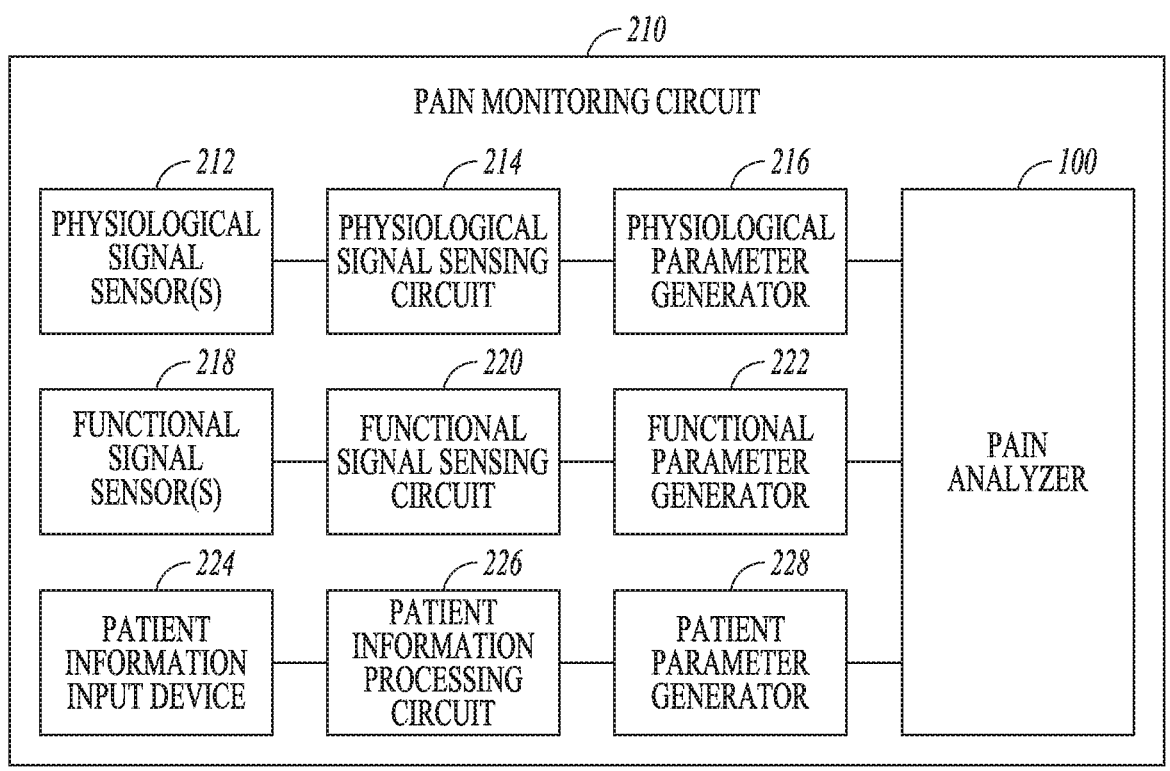
FIG. 2 illustrates an embodiment of a pain monitoring circuit including a pain analyzer such as the pain analyzer of FIG. 1.

FIG. 2 illustrates an embodiment of a pain monitoring circuit 210. In the illustrated embodiment, pain monitoring circuit 210 includes one or more physiological signal sensors 212, a physiological signal sensing circuit 214, a physiological parameter generator 216, one or more functional signal sensors 218, a functional signal sensing circuit 220, a functional parameter generator 222, a patient information input device 224, a patient information processing circuit 226, a patient parameter generator 228, and pain analyzer 100. In various embodiments, pain monitoring circuit 210 can include at least one or more physiological signal sensors 212, physiological signal sensing circuit 214, physiological parameter generator 216, one or more functional signal sensors 218, functional signal sensing circuit 220, functional parameter generator 222, and pain analyzer 100.

In various embodiments, one or more physiological signal sensors 212 can each sense one or more physiological signals, and can each be a non-invasive, percutaneous, or implantable sensor. Physiological signal sensing circuit 214 can process the one or more physiological signals. Physiological parameter generator 216 can generate the one or more physiological parameters using the processed one or more physiological signals. Examples of the one or more physiological parameters can include one or more measures of physiologic manifestations of change in the patient's sympathetic activity (referred to as "autonomic measures"), one or more direct measures of neuronal activity (referred to as "neuron/brain measures"), and/or one or more chemical or analyte parameters derived from body tissue, fluid, and/or excretion collected from the patient.

Examples of the one or more autonomic measures can include (1) heart rate and heart rate variability, including time and frequency domain measures, statistic metrics in the time domain including standard deviation of the baseline normal R-R intervals to assess changes from baseline, the square root of mean squared differences of successive R-R intervals over different time windows, q-factors for spectral peaks at very low frequency (VLF), low frequency (LF), and high frequencies (HF), ratio of power in the different frequency bands (LF/HF), changes in frequency of maximum peaks over time, and complexity metrics derived from these signals; (2) blood pressure measures including systolic and diastolic blood pressure, pulse transit time, wave amplitude, and volume (the blood pressure measures can be obtained using heart sounds such as by leveraging the second heart sound (S2) as a strong surrogate for pressure readings through either invasive or noninvasive means, or can also be acquired using blood pressure cuffs or photoplethysmograms (PPGs)); and (3) galvanic skin response, including time and frequency domain measures. Additional examples of the one or more autonomic measures can be found in Table 1 (e.g., under "Autonomic Measures"). Examples of the neuron/brain measures can include (1) electroencephalogram (EEG) based pattern analysis and frequency domain measures; (2) electromyogram (EMG) based time (amplitude and latency) and frequency domain measures; and (3) response to specific evoked potentials (EPs) that are affected under cognitive tasks, mental state changes, mood variation, presence of depression, and/or presence of different levels of pain. Additional examples of the one or more neuron/brain measures can be found in Table 1 (e.g., under "Neuron/Brain Measures"). In various embodiments, physiological parameter generator 216 can generate any one or any combination of these examples as the one or more physiological parameters. Examples of the one or more chemical or analyte parameters can include parameters derived from the patient's blood, sweat, saliva, breath, tissue, etc. Additional examples one or more chemical or analyte parameters can be found in Table 1 (e.g., under "Biochemical Measures").

In various embodiments, one or more functional signal sensors 218 can sense one or more functional signals, and can each be a non-invasive, percutaneous, or implantable sensor. Functional signal sensing circuit 220 can process the one or more functional signals. Functional parameter generator 222 can generate the one or more functional parameters using the processed one or more functional signals. Examples of the one or more functional signals can include measures of (1) movement (e.g., activity level, gait pattern, range of motion, or sleep) and (2) posture. Additional examples of the one or more functional parameters can be found in Table 1 (e.g., under "Functional Measures"). In various embodiments, physiological parameter generator 222 can generate any one or any combination of these examples as the one or more functional parameters.

In various embodiments, patient information input device 224 can receive patient information related to pain. Patient information processing circuit 226 can process the patient information. Patient parameter generator 228 can generate one or more patient parameters using the processed patient information. Examples of the one or more patient parameters can (1) parameters derived from input from the patient such as perceived pain levels, mood, and stress levels (including external interactions, such as interactions with another person) as a way to quantify non-physical activity); and (2) parameters derived from the patient's medical history record (e.g., demographic data, diagnoses, procedures applied, and prescriptions). Some additional examples of the parameters derived from the patient's medical history record can be found in Table 1 (e.g., under "Biochemical Measures"). In various embodiments, patient parameter generator 228 can generate any one or any combination of these examples as the one or more patient parameters.

Figure 3:
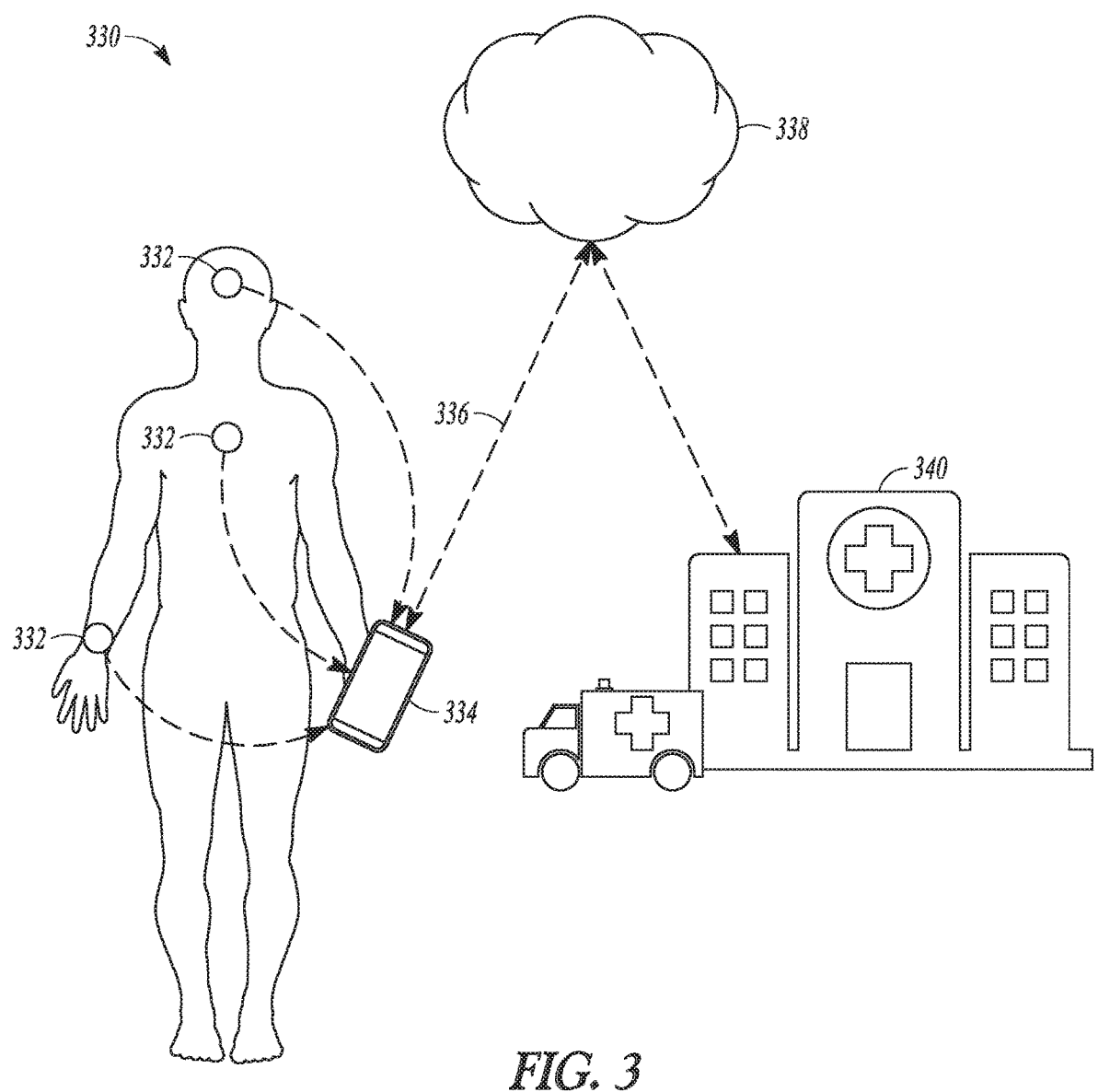
FIG. 3 illustrates an embodiment of a pain management system and portions of an environment in which the system operates.

FIG. 3 illustrates an embodiment of a pain management system 330 and portions of an environment in which system 330 operates. System 330 can include sensors 332, a portable device 334, a network 338 communicatively coupled to portable device 334 via a communication link 336, and a medical facility 340 communicatively coupled to network 338. A pain monitoring circuit such as pain monitoring circuit 210 can be distributed in sensors 332 and portable device 334. In various embodiments, portable device 334 can be implemented as a dedicated device or in a generic device such as a smartphone, a laptop computer, or a tablet computer.

For example, sensors 332 may include at least one sensor of physiological sensor(s) 212 and one sensor of functional signal sensor(s) 218, and portable device 334 can include the remaining components of pain monitoring circuit 210. The composite pain score as well as other data acquired by portable device 334 can be transmitted to network 338 via communication link 336 to be stored, further analyzed, and/or inform the patient's healthcare provider. When the composite pain score and/or the other data indicate that the patient needs medical attention, a notification will be transmitted to medical facility 340 from network 338. In various embodiments, sensor(s) 332 can include external, percutaneous, and/or implantable sensors that communicate with portable device 334 via wired and/or wireless links, and communication link 336 can be a wired or wireless link.

Figure 4:
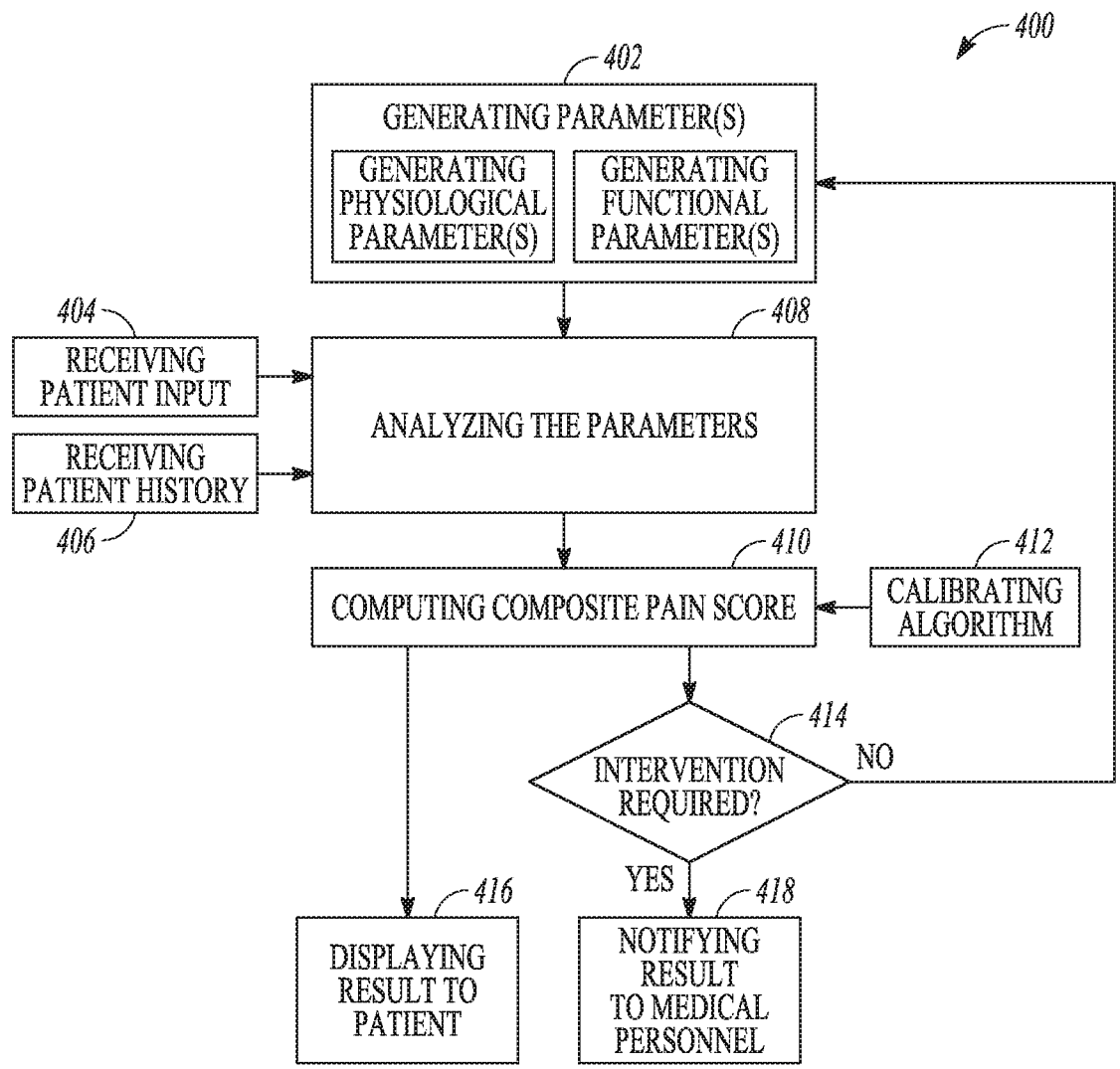
FIG. 4 illustrates an embodiment of a method for pain management such as may be performed by the pain management system of FIG. 3.

FIG. 4 illustrates an embodiment of a method 400 for pain management. In one embodiment, system 330 is configured to perform method 400 for a patent.

At 402, one or more physiological parameters and one or more functional parameters are generated. The one or more physiological parameters are each indicative of a physiological function or state of the patient. The one or more functional parameters are each indicative of a physical activity or state of the patient. Examples of such one or more physiological parameters can include the physiological parameters that can be generated by physiological parameter generator 216 as discussed above with reference to FIG. 2 and Table 1. Examples of such one or more functional parameters can include the functional parameters that can be generated by functional parameter generator 222 as discussed above with reference to FIG. 2 and Table 1.

Optionally at 404, patient input is received. Optionally at 406, patient history is received. The received patient input and/or patient history include one or more patient parameters related to the pain of the patient. Examples of such one or more patient parameters can include the patient parameters that can be generated by patient parameter generator 228 as discussed above with reference to FIG. 2 and Table 1. In various embodiments, the one or more patient parameters can include one or more parameters directly entered by the patient or another person attending the patient as well as one or more parameters derived from information entered by the patient or another person attending the patient and the patient's medical history. In one embodiment, the one or more patient parameters includes a parameter representative of intensity of the pain specified by the patient based on his or her perception of the pain.

At 408, the parameters generated and/or received at 402, 404, and 406 are analyzed. In various embodiments, the analysis can result in a signal metric using one or more physiological parameters, one or more functional parameters, and/or the one or more patient parameters. In one embodiment, the analysis results in the signal metric using at least one parameter selected from the one or more physiological parameters, the one or more functional parameters, or the one or more patient parameters. In one embodiment, the analysis results in the signal metric using at least two parameters selected from the one or more physiological parameters, the one or more functional parameters, or the one or more patient parameters. In one embodiment, the analysis results in the signal metric using at least one physiological parameter and one functional parameter. In one embodiment, the analysis results in the signal metric using at least two parameters selected from a physiological parameter, a functional parameter, and a patient parameter. In one embodiment, the analysis results in the signal metric using the one or more physiological parameters and the one or more functional parameters. In one embodiment, the analysis results in the signal metric using the one or more physiological parameters and the one or more patient parameters. In one embodiment, the analysis results in produces the signal metric using the one or more functional parameters and the one or more patient parameters. In one embodiment, the analysis results in produces the signal metric using the one or more physiological parameters, the one or more functional parameters, and the one or more patient parameters.

In various embodiments, weighting factors can be generated, and the signal metric can be produced using the one or more physiological parameters, the one or more functional parameters, and/or the one or more patient parameters with the weighting factors each applied to one of these parameters. In another embodiment, one or more of the one or more physiological parameters, the one or more functional parameters, and the one or more patient parameters are preprocessed to extract relevant pain information features before generating the weighting factors to be applied to these features. In another embodiment, the weighting factors are generated using one or more machine learning techniques such as neural network, fuzzy logic, support vector machines, and/or generalized linear or non-linear regressions.

At 410, a composite pain score is computed. In various embodiments, the composite pain score can be computed using the signal metric. In various embodiments, additional parameters such as environmental parameters and time can be used in computing the composite pain score, such as by including in the analysis that results in the signal metric. The environmental parameters, such as temperature, humidity, and/or air pressure, may influence discernment of pain. In various embodiments, such environmental parameters can be measured by system 300 and/or obtained from weather forecasts based on location (e.g., specified manually or using a global positioning system) to anticipate or predict their impact to the composite pain score. One or more weighting factors can be determined based on the reliability of these environmental parameters (e.g., depending on how they are obtained) and applied in computing the composite pain score. Time of day may capture circadian influence on pain. There are still additional parameters that can affect pain, and can be used in computing the composite pain score, such as by including in the analysis that results in the signal metric. Examples can include, but are not limited to, amount and/or quality of sleep (e.g., as measured by system 330), amount and/or type of activity during a preceding period of time (e.g., the previous day or week, and measured by system 330), personal events that may have positive impact or negative impact on pain, medication changes, time of year (e.g., birthday and holidays), personal events that may have positive impact or negative impact on pain (e.g., church and socialization activities making for consistent good moods on Sunday with a let down on Monday, as monitored and recognized as a pattern by system 330), and/or deviation from patterns determined by system 330 (e.g., regular activity around lunch time because walking to a cafeteria stops due to changes in pain perception not identified by other parameters). In one embodiment, the signal metric is trended, and the composite pain score is computed based on the trend.

At 412, the algorithm used to compute the composite pain score is calibrated. In various embodiments, the calibration can include adjusting the one or more weighting factors manually, automatically by learning and adapting to the patient's circumstances and conditions over time, and/or adjusting the weighting factors based on changes in the physiological and functional parameters. The weighting factors can be adjusted according to a calibration schedule or as needed. In various embodiments, the calibration can be a continuous process. For example, calibration can be performed over the course of minutes or longer, e.g., days, to encompass a range of activities. Calibration can be a prompted activity or scheduled to occur intermittently, for example. Different weighting factors can be used for various activities, such as sleeping and walking. In various embodiments, the weighting factor can be linear or non-linear in nature.

At 414, whether medical intervention is required is determined, such as by comparing the composite pain score to one or more thresholds. If intervention is not required as determined at 414, the one or more physiological parameters and one or more functional parameters are generated again (i.e., their values are updated) for continued monitoring of the patient.

At 416, the result of the computation, including at least the composite pain score, is displayed to the patient or a caregiver. At 418, if intervention is required as determined at 414, relevant medical personnel is notified for appropriate action that can be dependent on the composite pain score. Examples of the appropriate action can include instructing the patient to take medication, instructing the patient to visit a clinic, or sending medical personnel to visit the patient.

Figure 5:
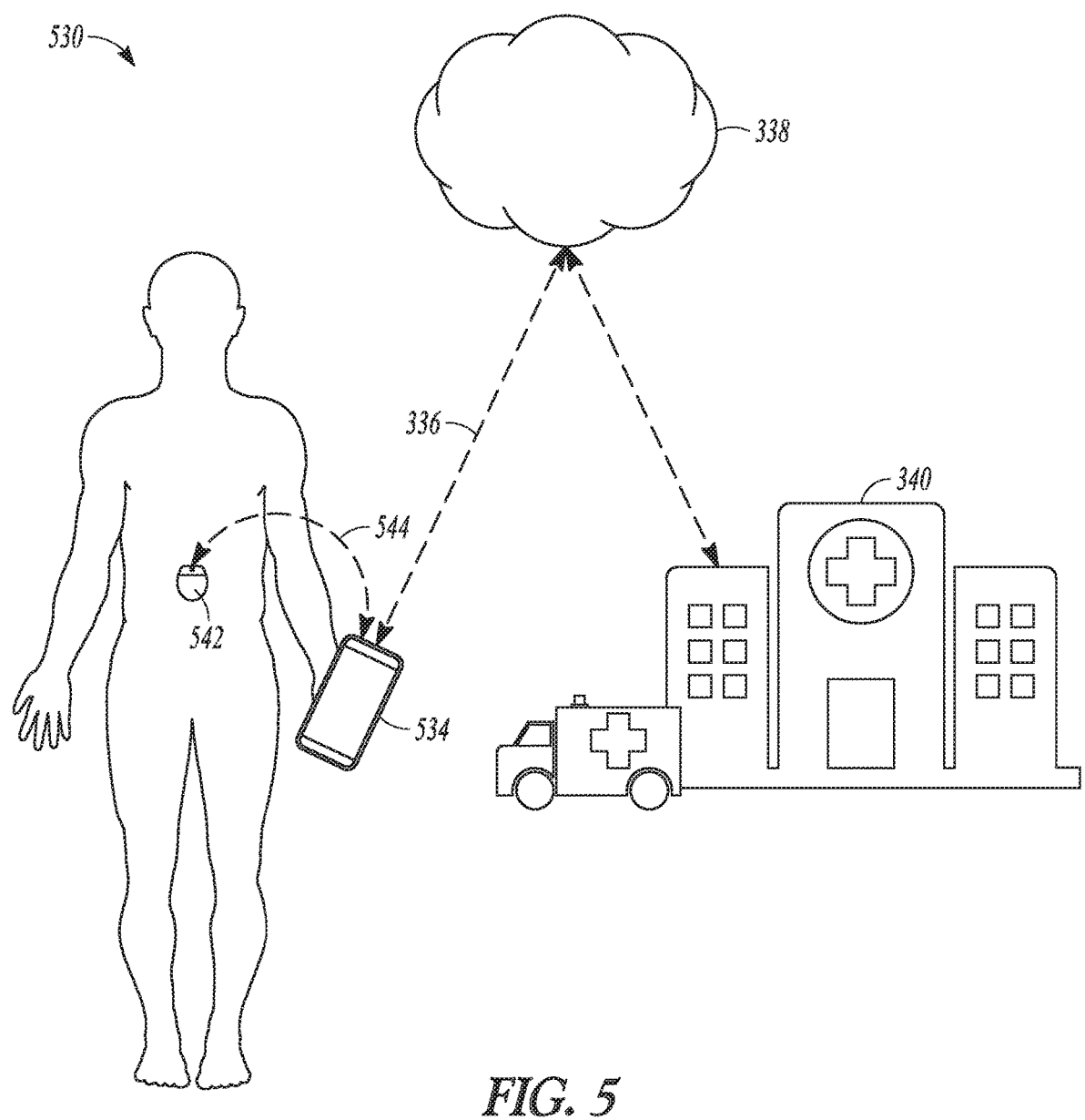
FIG. 5 illustrates another embodiment of a pain management system and portions of an environment in which the system operates.

FIG. 5 illustrates another embodiment of a pain management system 530 and portions of an environment in which system 530 operates. System 530 can include an implantable medical device 542, a portable device 534 communicatively coupled to implantable medical device 542 via a wireless communication link 544, network 338 communicatively coupled to portable device 534 via communication link 336, and medical facility 340 communicatively coupled to network 338. A pain monitoring circuit such as pain monitoring circuit 210 can be distributed in implantable medical device 542 and portable device 534, and implantable medical device 542 can deliver one or more pain relief therapies. In various embodiments, portable device 534 can be implemented as a dedicated device or in a generic device such as a smartphone, a laptop computer, or a tablet computer.

For example, implantable medical device 542 may include at least one sensor of physiological sensor(s) 212 and one sensor of functional signal sensor(s) 218, and portable device 534 can include the remaining components of pain monitoring circuit 210. The composite pain score as well as other data acquired by portable device 534 can be transmitted to network 338 via communication link 336 to be stored, further analyzed, inform the patient's healthcare provider, and/or used to control delivery of one or more pain relief therapies from implantable medical device 542. When the composite pain score and/or the other data indicate that the patient needs medical attention, such as when system 530 is unable to automatically adjust the one or more pain relief therapies for a satisfactory result as indicated by the composite pain score, a notification will be transmitted to medical facility 340 from network 338.

Figure 6:
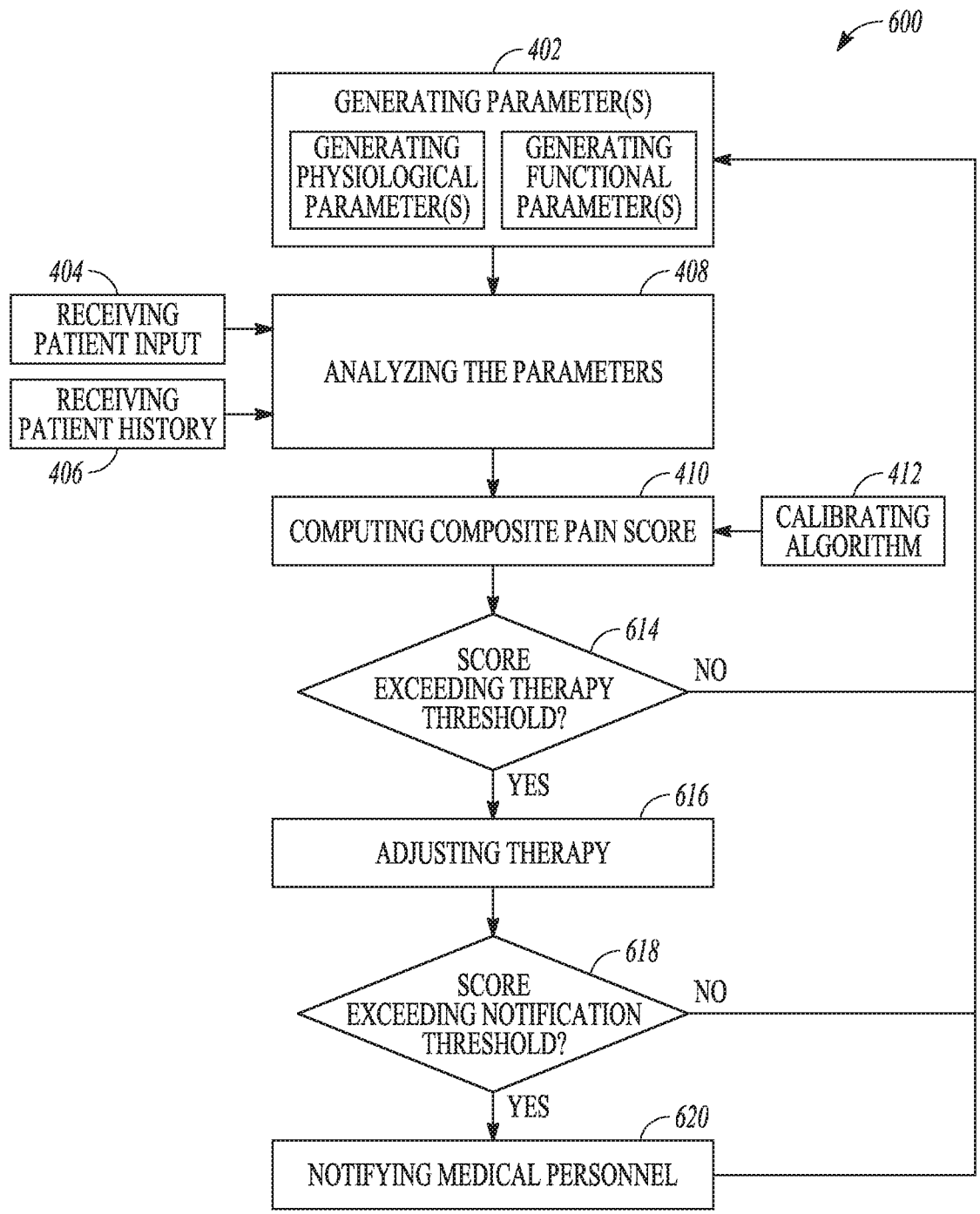
FIG. 6 illustrates an embodiment of a method for pain management such as may be performed by the pain management system of FIG. 5.

FIG. 6 illustrates an embodiment of a method 600 for pain management. In one embodiment, system 530 is configured to perform method 600 for a patent. Method 600 can be performed for monitoring pain of the patient and delivering one or more pain relief therapies to the patient with closed-loop control. As illustrated in FIG. 6, method 600 includes steps 402, 404, 406, 408, 410, and 412 of method 400.

At 614, the composite pain score is compared to a therapy threshold indicating a need for adjusting a pain relief therapy. If the composite pain score does not exceed the therapy threshold as determined at 614, the one or more physiological parameters and one or more functional parameters are generated again (i.e., their values are updated) for continued monitoring of the patient. Examples of the pain relief therapy can include neuromodulation therapies (e.g., SCS, PNS, DBS, and TMS) and drug therapies.

At 616, when the composite pain score exceeds the therapy threshold as determined at 614, the pain relief therapy is adjusted. The adjustment can include starting a therapy, increasing intensity (e.g., neurostimulation energy or drug dose), switching to a different type therapy, or adjusting any therapy parameters. Examples of therapy parameters for various types of neuromodulation therapies can include pulse frequency, burst frequency, pulse width, waveform shape, anode/cathode configurations, and current fractionalization.

At 618, whether the composite pain score exceeds a notification threshold is determined. At 620, if the pain exceeds the notification threshold as determined at 618, relevant medical personnel is notified for appropriate action that may be dependent on the composite pain score and/or the record of delivery of the pain relief therapy. Examples of the appropriate action can include instructing the patient to take medication, instructing the patient to visit a clinic, or sending medical personnel to visit the patient. If the pain does not exceed, the notification threshold as determined at 618, no notification to relevant medical personnel is necessary. In any case, the one or more physiological parameters and one or more functional parameters are continued to be generated (i.e., their values are updated) for continued assessment of the patient pain level.

Figure 7:
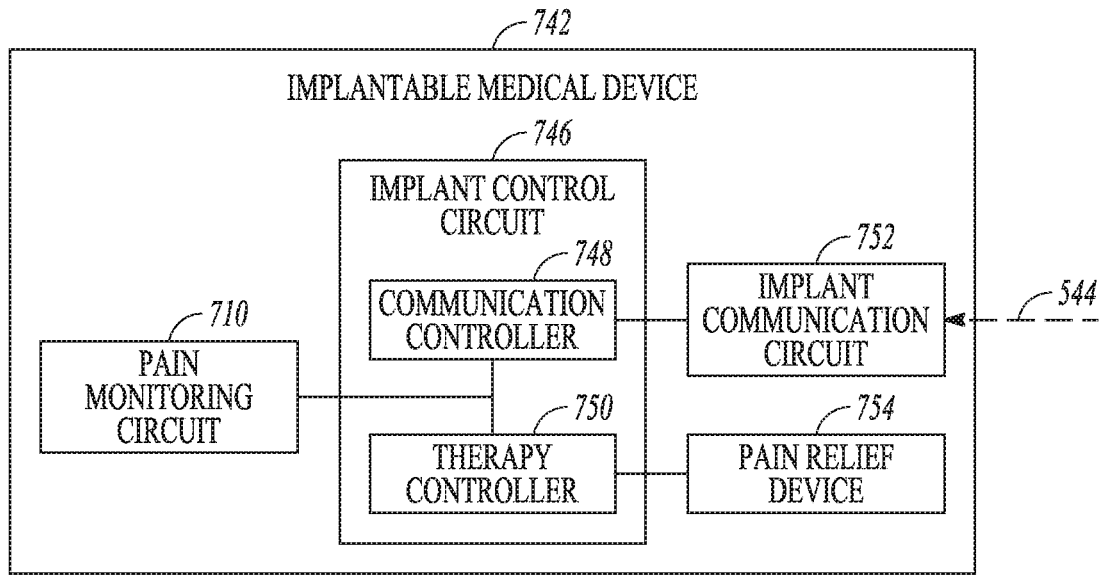
FIG. 7 illustrates an embodiment of an implantable medical device of a pain management system such as the pain management system of FIG. 5.

FIG. 7 illustrates an embodiment of an implantable medical device 742, which represents an example of implantable medical device 542. Implantable medical device 742 can include a pain monitoring circuit 710, an implant communication circuit 752, and a pain relief device 754. Pain monitoring circuit 710 represents an example of pain monitoring circuit 210 as implemented in an implantable medical device. When the one or more patient parameters are used by pain analyzer 100, patient information input device 224 can receive the patient information from an external device communicatively coupled to implantable medical device 742 via communication link 544.

Implant control circuit 746 controls the operation of implantable medical device 742 and can include a communication controller 748 and a therapy controller 750. Communication controller 748 can control transmission of the composite pain score the external device, such as on a periodical basis or according to another specified schedule, when the composite pain score exceeds a specified threshold, when change in the composite pain score exceeds a specified threshold, or when the rate of change in the composite pain score exceeds a specified threshold. Therapy controller 750 can control the delivery of the one or more pain-relief therapies using the composite pain score and therapy parameters. Implant communication circuit 752 allow implantable medical device 742 to communicate with the external device via communication link 544. Pain relief device 754 can deliver one or more pain-relief therapies. In various embodiments, pain relief device 754 can include a neuromodulator to deliver electrical stimulation (such as SCS, PNS, DBS, and/or TMS) and/or a drug pump to deliver one or more pain suppression agents.

Figure 8:
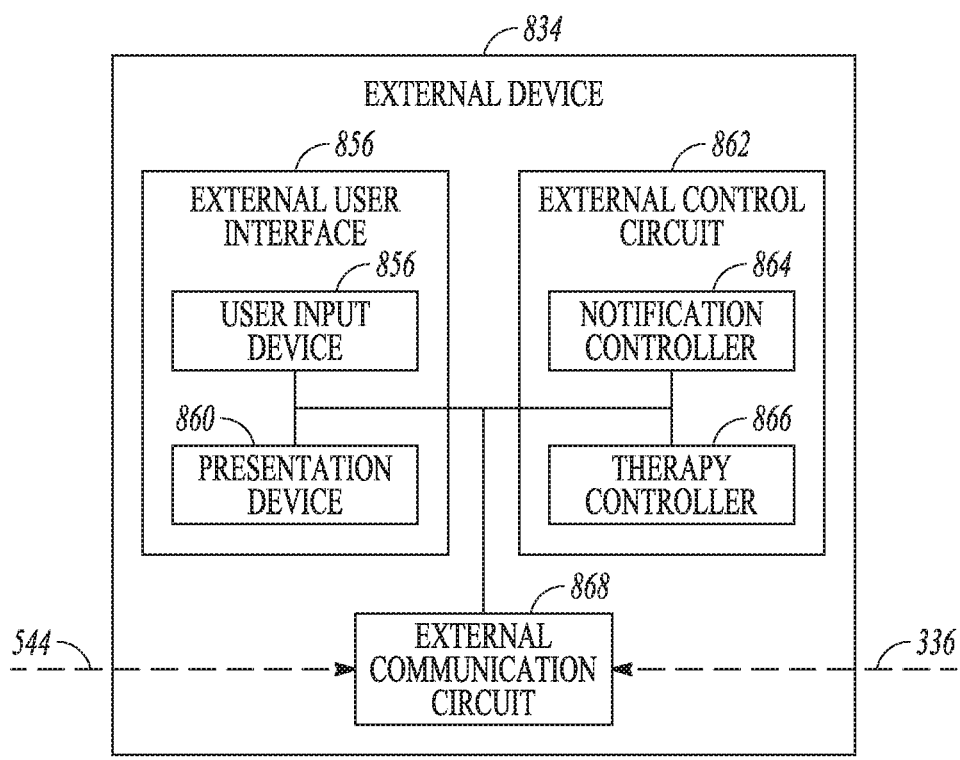
FIG. 8 illustrates an embodiment of an external device of a pain management system such as the pain management system of FIG. 5.

FIG. 8 illustrates an embodiment of an external device 834, such as may be implemented in portable device 534. External device 834 can include an external user interface 856, an external control circuit 862, and an external communication circuit 868. In various embodiments, external device 834 can be implemented in a portable device such as a hand-held or wearable device.

External user interface 856 can include a user input device 858 and a presentation device 860. User input device 858 can receive patient information such as a subjective input from the patient to indicate the degree of the pain as perceived by the patient. Presentation device 860 can include a display screen and/or other audio and/or visual presentation devices. In one embodiment, a touchscreen is used as user input device 858 and presentation device 860. External control circuit 862 controls operation of external device 834 and can include a notification controller 864 and a therapy controller 866. Notification controller 864 can receive the composite pain score from implantable medical device 742, produce a notification using the composite pain score, determine one or more recipients of the notification using the composite pain score, and control delivery of the notification to each of the one or more recipients. The recipients can include the patient and/or various users of a pain management system such as system 530. In various embodiments, notification controller 864 can present the notification using presentation device 860. The notification can include the composite pain score, one or more indicators representing the pain score, an alert or alarm message regarding the patient's pain state, and/or instructions for actions to be taken by the patient. In various embodiments, notification controller 864 can produce and present the notification when the composite pain score exceeds a specified threshold, when change in the composite pain score exceeds a specified threshold, or when the rate of change in the composite pain score exceeds a specified threshold. Therapy controller 866 can produce external commands for adjusting the therapy parameters using the composite pain score and the patient information and transmit the external commands to implantable medical device 742 via communication link 544. External communication circuit 868 allow external device 834 to communicate with implantable medical device 742 via communication link 544 and to communicate with a remote device via communication link 336.

Figure 9:
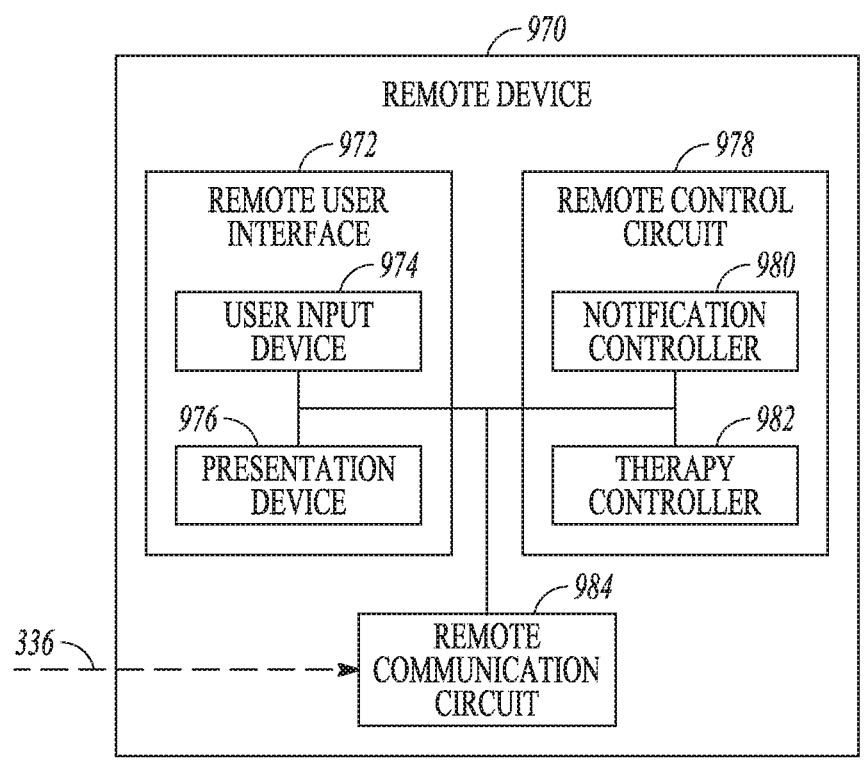
FIG. 9 illustrates an embodiment of a remote device of a pain management system such as the pain management system of FIG. 5.

FIG. 9 illustrates an embodiment of a remote device 970, such as may be implemented in network 338 and/or medical facility 340. Remote device 970 can be used for patient monitoring and therapy control, and can include a remote user interface 972, a remote control circuit 978, and a remote communication circuit 984.

Remote user interface 972 can include a user input device 974 and a presentation device 976. User input device 974 can receive patient information such as patient history stored in network 338 and/or medial facility 340, and can also receive user commands for adjusting the one or more pain-relief therapies. Such user command may be determined based on updated knowledge about the patient's conditions and/or results of one or more pain-relief therapies received by the patient. Presentation device 976 can include a display screen and/or other audio and/or visual presentation devices. In one embodiment, a touchscreen is used as user input device 974 and presentation device 976. Remote control circuit 978 can include a notification controller 980 and a therapy controller 982. Notification controller 980 can receive the notification transmitted from external device 834, determine one or more further recipients of the notification, and control delivery of the notification to each of the one or more further recipients. Such further recipients can include physicians and/or other caregivers attending the patient, a hospital, and a medical emergency response facility. Therapy controller 982 can produce remote commands for adjusting the delivery of the one or more pain-relief therapies using the notification and the user commands. In various embodiments, therapy controller 866 of external device 834 can produce the external commands using the composite pain score, the patient information, and the remote commands. Remote communication circuit 984 can communicate with external device 834 via communication 336 and network 338.

In various embodiments, circuits of the present pain management system, including its various embodiments discussed in this document, may be implemented using a combination of hardware and software. For example, the circuits may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

TABLE 1

Parameters indicative of level of pain.

| Bio-marker (Parameter) | Physiology/Definition | Signals Sensed (Examples only) | References |
|---|---|---|---|
| Autonomic Measures | | | |
| Heart Rate (HR) | Indicator of sympathetic tone. Higher HR indicates higher sympathetic nervous activity (SNA) | ECG, PPG | 1, 2 |
| Heart Rate Variability (HRV) | Measure of autonomic balance. Autonomic dysfunction at the base of many disease states. Appears to be a reliable marker for adaptive stress, including both dynamic and cumulative load. Acute stress and chronic stress both lower HRV | ECG, PPG- | 3, 4, 5, 6, 7, 8, 9, 10 |
| AVNN | Average of all NN intervals | ECG, PPG | |
| SDINTNT | Standard deviation of all NN intervals (Measure of long term HRV) | ECG, PPG | |
| SDANN | Standard deviation of the averages of NN intervals in all 5-minute segments of a 24-hour recording (Measure of long term HRV) | ECG, PPG | |
| SDNNIDX | Mean of the standard deviations of NN intervals in all 5-minute segments of a 24-hour recording | ECG, PPG | |
| RMSSD | Square root of the mean of the squares of differences between adjacent NN intervals. (Measure of short term HRV) | ECG, PPG | |
| pNN50 | Percentage of differences between adjacent NN intervals that are greater than 50 ms. | ECG, PPG | |
| vLF | Total spectral power of all NN intervals between 0.003 and 0.04 Hz | ECG, PPG | |
| LF | Total spectral power of all NN intervals between 0.04 and 0.15 Hz | ECG, PPG | |

TABLE 1-continued

Parameters indicative of level of pain.

| Bio-marker (Parameter) | Physiology/Definition | Signals Sensed (Examples only) | References |
|---|---|---|---|
| HF | Total spectral power of all NN intervals between 0.15 and 0.4 Hz | ECG, PPG | |
| LF/HF | Ratio of low to high frequency power | ECG, PPG | |
| total power | total spectral power of al NN intervals up to 0.4 Hz | ECG, PPG | |
| UsEn | Ultra-short entropy (UsEn) is a nonlinear approach that is thought to offer an insight into the overall structure of the RR regulatory system with a connection between disorder and a decrease in entropy | ECG, PPG | |
| alpha 1 | Short term fractal scaling exponent measures the qualitative characteristics and correlation features of HR behavior. | ECG, PPG | |
| Galvanic Skin Response (GSR) | SNA causes sweat glands to fill up and skin conductance increases creating skin conductance fluctuations. | Electrodes on the hand, measure conductivity | 11, 12, 13, 14 |
| Photo-Plethysmographic (PPG) | Reduction in the amplitude of PPG is caused by peripheral vasoconstriction and the nociception response during general anesthesia. Vasoconstriction as a result of increased SNA. | PPG | 15, 16, 17, 18 |
| Pulse Rate Variability (PRV) | Could be a replacement measure for HRV. Can be used to estimate HRV at rest. | PPG | 19, 20, 21 |
| Blood Pressure (BP) | Marker of sympathetic ton. Increased ton causes vasoconstriction and thus elevated BP. Increased BP is associated with increased pain levels | PPG | 22, 23 24, 25 |
| Pulse Transit Time & Pulse Wave Amplitude (Alternative measure for BP) | Vasoconstriction is a physiological response to pain which directly impacts the pulse transit time and pulse wave amplitude. In the presence of painful stimuli, both pulse transit time and pulse wave amplitude decrease. | PPG, possible internal sensor (at 2 locations to measure transit time) | 26, 27, 28 |
| Respiration Rate (RR) | Measure of sympathetic tone. Elevated respiratory rate corresponds to increased pain. | ECG, embedded strain gauge | 29, 30, 31, |
| Pupil Diameter | Dilation of the pupil is indicative of sympathetic activation | *Imaging | 32 |
| Respiratory Sinus Arrhythmia (RSA) | RSA is a physiological indicator that may have implications for responses to pain and stress. It is essentially the transfer function from respiration rate to R-R intervals. Another way to assess cardiac autonomic function. Pain is associated with an impairment of neurocardiac integrity which can be measured through RSA which decreases in the presence of increased sympathetic activity / decreased parasympathetic activity. | | 33, 34, 35, 36, 37 |
| Baroreceptor Sensitivity | Increased baroreceptor response is associated with decreased pain levels. | BP monitoring | 38, 39, 40, 41, 42, 43, 44, 45, 46, 47 |
| Normalized Pulse Volume (NPV) | Sympathetic tone causes vascular constriction. This vascular tone can be measured in several locations on the body to indicate sympathetic tone. NPV can be derived from the fingertip using PPG. It can also be derived from the bottom of the ear canal. | Measured in the outer ear or at the finger tip | 48, 49 |
| Functional Measures | | | |
| Activity | Measuring activity in patients with pain can be an indicator of pain | Accelerometer | 50, 51, 52 |

TABLE 1-continued

Parameters indicative of level of pain.

| Bio-marker (Parameter) | Physiology/Definition | Signals Sensed (Examples only) | References |
|---|---|---|---|
| | level with patients in severe pain participating in less activity | | |
| Timed up-and-go | Faster up-and-go time :shorter time to complete task), less discomfort and able to move more quickly. | Accelerometer | |
| Physical activity | Increased physical activity is a sign of decreased discomfort | Accelerometer | |
| Gait | Patients with pain may have altered gait due to pain, such as a limp. | Accelerometer gyroscope | 53, 54, 55, 56, 57, 58, 59, 60, |
| Velocity | set distance to walk divided by time it takes to walk the set distance | Accelerometer gyroscope | |
| Stride Length | linear distance between the placement of both feet | Accelerometer/ gyroscope | |
| Swing Time | time from the moment the foot lifts from the floor until it touches again | Accelerometer/ gyroscope | |
| Single Limb Support Time | time from when the heel touches the flood until toes are lifted | Accelerometer/ gyroscope | |
| Gait autonomy | maximum time a person can walk, taking into account the number and duration of stops | Accelerometer/ gyroscope | |
| Trunk-Pelvis Rotation, balance | Altered gait patterns are observed in patients with pain. Due to pain/discomfort, the coordination of the trunk and pelvis rotations vary from healthy subjects. In a healthy person, pelvis-thorax coordination in the transverse plane evolves gradually from in-phase coordination towards antiphase coordination with increasing walking velocity. In patients with pain these movements are more rigid and less flexible coordination. | Gyroscope | |
| Facial expressions | Particular facial expressions/cues are associated with pain (Facial Action Units) such as nose wrinkling and cheek-raising | Imaging | 61 |
| Sleep Quality | Poor sleep quality is often observed when patients are in pain. More movement and wakefulness during sleep. | accelerometer, subjective | 62, 63, 64, 65 |
| Quality of Life/Mood (Can be subjective or objective) | Quality of life/mood can affect pain score. Better mood can decrease pain perception/intensity | subjective | 66 |
| Stress - Subjective measure | Stress levels can greatly affect HRV and sympathetic tone. | ECG (HRV), subjective | 67, 68, |

Neuron/Brain Measures

| Quantitative Sensory Test (QST) | Method used to assess damage to the small nerve endings, which detect changes in temperature, and large nerve endings, which detect vibration | Neurometer | 69, 70, 71, 72, 73, 74, 75, 76 |
|---|---|---|---|
| Warm | Heat stimuli, subject reports temperature change or heat pain threshold | Neurometer | |
| Cold | Cold stimuli, subject reports temperature change or cold pain threshold | Neurometer | |
| Vibration | Measure sensation/sensitivity to vibration. Set frequency and change amplitude to detect threshold/sensitivity | Neurometer | |
| Current Perception Threshold (CPT) | Also known as sensory nerve conduction threshold testing. Entails the quantification of the sensory threshold to transcutaneous electrical stimulation. CPT measure represents the minimal amount of painless, neuroselective transcutaneous electrical stimulus required to reproducibly evoke a sensation. | Neurometer | |
| Pain Perception Threshold (PPT) | PPT represents the minimum current intensity that produced pain | Neurometer | |

TABLE 1-continued

Parameters indicative of level of pain.

| Bio-marker (Parameter) | Physiology/Definition | Signals Sensed (Examples only) | References |
|---|---|---|---|
| Pain Tolerance Threshold (PTT) | PTT measure is the maximum amount of neuroselective electrical stimulus that a subject can tolerate | Neurometer | |
| Tactile Discrimination Threshold | Stimulation of the index finger with assessments of 2-point discrimination thresholds as a marker for tactile perception. | Neurometer | |
| EEG | Increased activity in the pain matrix of patients in a high pain state versus low pain state | EEG | 77, 78, 79, 80 |
| Spectral Power | Increased spectral power is attributable to theta over activity. | EEG | |
| Dominant Frequency (DF) | Increased peak height and decreased DF due to slowed rhythmicity in EEG in neuropathic pain. | EEG | |
| (Contact) Heat EPs | Uses rapidly delivered heat pulses with adjustable peak temperatures to stimulate the differential heat/warm thresholds of receptors expressed by the A-delta and C. Believed to be composed of at least 2 overlapping components. Some theorize that it reflects the degree of discomfort or unpleasantness thus reflecting the emotional-motivational aspect Provides a useful neurophysiologic tool for studying the emotions associated with pain | EEG | 81, 82, 83, 84 |
| Somatosensory EPs | Electrical signal is nervous system in response to a sensory stimuli. Consists of a series of waves that reflect sequential activation of neural structures along somatosensory pathways | EEG | |
| EMG | Reflect endogenous processing of pain information in response to external stimuli. | EMG | |
| Neurophysical test | P40-SEP amplitude, H-reflex amplitude, Rill reflex threshold, and RIII reflex area. Neurophysical tests detect and record the electrical potential generated by muscle cells when they are activated. These signals can be analyzed to detect medical abnormalities or to analyze the biomechanics of movement. | EMG, Reporter EMG-EP machine | 85 |
| Spinal Stability, Lumbar EMG | EMG activity is elevated in low back pain patients especially during dynamic movements. This increased could be due to restricted range of motion and/or a compensatory mechanism to maintain stability. It is widely accepted that there is a relationship between pain, stiffness, and muscle activity in low back pain patients. | EMG, sEMG (surface EMG) | 86, 87, 88, 89, 90, 91, 92 |
| Nociceptive Flexion Reflex / Nociceptive Withdrawal Reflex | Nociceptive flexion reflex (NM.) is a physiological, polysynaptic reflex allowing for painful stimuli to activate an appropriate withdrawal response. To capture this response, the sural nerve is stimulated and the EMG response is recorded at the bicep femoris muscle. This stimulation elicits 2 reflex responses: (1) RII reflex which has a short latency, low activation threshold, and is a tactile reflex and (2) RIII reflex which has a longer latency, higher activation threshold, and is the nociceptive reflex. RIII is the focus of the NFR correlations with pain. The measured parameter | sEMG on the bicep femoris muscle | 93, 94, 95, 96, 97 |

TABLE 1-continued

Parameters indicative of level of pain.

| Bio-marker (Parameter) | Physiology/Definition | Signals Sensed (Examples only) | References |
|---|---|---|---|
| | is the NTR threshold (amplitude of stimulation necessary to activate RIII) for activation, which has shown to directly correlate to perceived pain. | | |
| MSNA | Muscle sympathetic nerve activity. Variance in MSNA may be associated with cardiac output with a negative relationship observed between MSNA and cardiac output. MSNA can influence FIRV. MSNA could be used as an indicator of autonomic activity. | EMG | 98, 99, 100, 101 |
| Default-Mode Network (DMN) | Proposed theory is that long-term pain alters the functional connectivity of cortical regions known to be active at rest. In chronic pain patients, these regions are associated with more activity, unable to deactivate. | EEG, fMRI | 102, 103 |
| Gray Matter Volume | Pain can lead to long term changes in the brain including changes in the volume of gray matter. GMV changes are region dependent. Changes seen are not necessarily in regions of the brain correlated with pain | MRI | 104 105 |
| MEG Theta Activity (Power) | Increased total power in the theta range (7-9Hz) is associated with increased pain state | MEG | 106, 107 |
| MR Spectroscopy Metabolites | MRS can be used to detect alterations in the biochemistry in the brain associated with chronic pain - in regions associated with pain. Distinct patterns were observed between painful and painless states. | MR spectroscopy | 108 |
| | Biochemical Measures | | |
| Cytokine Profile | Increased pro-inflammatory cytokines and decreased anti-inflammatory cytokines can increase pain/discomfort | Blood draw | 109 |
| pro-inflammatory | TNFa - applied to peripheral nerve fibers in vitro and in-vivo experiments leads to increased electrical activity in patients with pain, Increased TNFa in the blood and thus endoneural environment might also lead to increased C-fiber activity and sensation of pain. 1L-2 - has shown both analgesic and algetic effects. Elevated levels associated with pro-algetic effect. | Blood draw | |
| anti-inflammatory | IL-4, IL-10. Roles in down regulating the production of pro-inflammatory cytokines. Heightened 1L-4 & IL-10 protein may reflect a natural analgesic system regulating the activity and sensitivity of the endogenous opioid system. | Blood draw | |
| Biochemical Markers | Neurotensin, oxytocin and cortisol levels were increased after intervention (cervical and spinal manipulation). This response occurred immediately after intervention and the differences between the intervention and control groups were gone at 2 hours after intervention MDA (malondialdehyde) is a marker of oxidative stress and is increased in pain states DMS (ditnethylsphingosine) is a | Blood draw | 110, 111, 112, 113 |

TABLE 1-continued

Parameters indicative of level of pain.

| Bio-marker (Parameter) | Physiology/Definition | Signals Sensed (Examples only) | References |
|---|---|---|---|
| | small molecule byproduct of cellular membranes in the nervous system. This study was performed in rats where elevated levels of DMS were seen in rats with neuropathic pain. Biochemical mechanismsof chronic pain and fatigue. Chronic pain subjects had a reduction in serum sodium, increase in levels of markers of tissue damage (ALT (alanine aminotrasaminate) and AST (aspartate aminotranskrase)) and an increase in the tyrosine: leucine ratio which represents alterations in protein turnover. Lactic acid and proteoglycans metabolic markers) | | |
| GABA | Evidence that (ABA transmission is involved in the inhibition of dysesthesia, allodynia, and other signs of neuropathic pain | — | 114 |
| P2X4 Receptor Expression Levels | After nerve injury P2X4 receptors are upregulated in spinal microglia by several factors at the transcriptional and translational levels increase HR and BP are associated with increased burst amplitude but not in all patients. May have implications for individual differences in CV consequences of CP. | — | 115 |
| Salivary neuropeptide / cytokine / hormone detection | Levels of interleukin (1L)1a, IL8, AgRP, cortisol, monocyte chemotactic protein-1 (MCP1), dynorphin A, prolactin, valine, proline, hypoxanthine, propionate, formate, and acetate in saliva samples could be used to distinguish between patients with and without pain. Hypothalamic-pituitary-adrenal (HPA) axis, one of the main bodily stress systems, function has been found to be reduced in chronic pain patients. Salivary cortisol is commonly used to assess HPA axis function. Epinephrine and norepinephrine levels could potentially be used. | Saliva | 116, 117 |
| glial cell-derived neurotrophic factor | Concentrations of glial cell-derived neurotrophic factor in cerebrospinal fluid (CSF) have been shown to be higher in neuropathic pain patients. | CSF | 119 |
| Neuropeptide ligand: nociceptin/orphanin (N/OFQ) | CSF levels of nociceptin/orphanin (N/OFQ) have been found to be lower in patients treated with morphine than those not being treated with morphine. | CSF | 120 |
| Structural nerve proteins | Patients with sciatica and lumbar disc herniation have shown high CSF levels of neurofilament protein and S-100 protein, which are indicators of axonal damage and Schwann cell injury. | CSF | 120 |
| Markers of collagen metabolism | Intervertebral disc damage has been shown to be correlated with an increase in collagen metabolism, which can be monitored using serum markers such as PICP and CTX. | Blood draw | 120 |
| cystatin C | Upregulation of cystatin C has been demonstrated in animal models of pain, and higher levels of cystatin C | CSF | 120 |

TABLE 1-continued

Parameters indicative of level of pain.

| Bio-marker (Parameter) | Physiology/Definition | Signals Sensed (Examples only) | References |
|---|---|---|---|
| Purines | has been found in CSF samples of patients in pain compared to those not in pain, Fibromyalgia patients show abnormal profile of purines in plasma based on activity of enzymes involved in purine metabolism (adenosine deaminase, dipeptidyl peptidase IV and prolyl endopeptidase). | Blood draw | 123 |
| Peripheral tissue markers | Peripheral pain mediators are released in response to damage or disease, and induce sensitization leading to chronic pain. Examples include: Prostanoids Cytokines TNFα and IL-1β Nerve growth factor (NGF) Chemokines including CCL2, CCL3, and CXCL5 | Blood draw, Tissue Biopsy | 121 |
| CNS plasticity markers | Central sensitization is another step in the process leading to chronic pain, and is mediated by NMDA receptors. | Blood draw; Tissue Biopsy | 121 |
| Gene Expression | Altered gene expression is associated with chronic pain. Affected genes include: Nociceptors e.g., Trp-V1, TrpA1, GABA-B1, 5-HT3A) Ion channels regulating nociceptor excitability (e.g., Nav1.8 and other sodium channel subunits, potassium channel subunits) Transmitters and modulators released centrally (e.g., substance P, BDNF, neuropeptide Y) μ-opioid receptor Genes involved in GABA synthesis (e.g., GAD65, GAD67, GABA-B1) Human genetic studies have shown a correlation between GTP cyclohydrolase 1 polymorphisms, which decrease tetrahydrobiopterin (BH4) levels, and reduced pain in patients. Furthermore, excessive BH4 is produced after nerve injury in mice, and blocking the BH4 production reduces hypersensitivity. | Blood draw; Tissue Biopsy | 121, 122 |
| Epigenetic modifications | Epigenetic modifications is associated with the development of chronic pain Histone acetylation Histone deacetylase (HDAC) inhibitors (compounds that prevent the removal of acetyl groups from histones) can mitigate symptoms in animal models of inflammatory diseases (e.g., arthritis, colitis, and hepatitis), has also been shown to have clinical benefits arthritis DNA methylation Methyl binding protein MeCP2 has been shown to promote abnormal upregulation of a group of genes in | Blood draw; Tissue Biopsy | 121 |

TABLE 1-continued

Parameters indicative of level of pain.

| Bio-marker (Parameter) | Physiology/Definition | Signals Sensed (Examples only) | References |
|---|---|---|---|
| | inflammatory pain conditions intervertebral disc degeneration, and the chronic pain associated with it, has been shown to correlate with increases in methylation at the SPARC gene promoter in both mice and humans. | | |
| REST | REST promoter binding is directly responsible for reduced expression of several genes known to be relevant for nociceptive processing in the DRG (e.g., μ-opioid receptor, Nav1.8, Kv4.3). | | |

TABLE 1

Abbreviations used in Table 1.

| | |
|---|---|
| BP | Blood Pressure |
| BPV | Blood Pressure Variability |
| CP | Chronic Pain |
| CPT | Current Perception Threshold |
| CV | Cardiovascular |
| EEG | Electroencephalography |
| EMG | Electromyography |
| EP | Evoked Potential |
| FM | Fibromyalgia |
| GSR | Galvanic Skin Response |
| HR | Heart Rate |
| HRV | Heart Rate Variability |
| LBP | Low Back Pain |
| MSNA | Muscle Sympathetic Nerve Activity |

TABLE 1-continued

Abbreviations used in Table 1.

| | |
|---|---|
| NPV | Normalized Pulse Volume |
| NS | Not significant |
| OPS | Objective Pain Score |
| PA | Plethysmogram Amplitude |
| PPG | Plethysmograin |
| PPT | Pain Perception Threshold |
| PTT | Pain Tolerance Threshold |
| QST | Quantitative Sensory Testing |
| RSA | Respiratory Sinus Arrhythmia |
| SC | Skin Conductance |
| SCS | Spinal Cord Stimulation |
| SNA | Sympathetic Nervous Activity |
| UsEn | Ultra-short Entropy |

TABLE 3

References cited in Table 1.

1. TERKELSEN, ASTRID J., et al., "Heart Rate Variability in Complex Regional Pain Syndrome during Rest and Mental and Orthostatic Stress", Anesthesiology, Vol. 116, No. 1, (January 2012), 133-146
2. HALLMAN, DAVID, et al., "Autonomic regulation, physical activity and perceived stress in subjects with musculoskeletal pain; 24-hour ambulatory monitoring", International Journal of Psychophysiology 86, (2012), 276-282
3. KOENIG-, JULIAN, et al., "Chronic Pain and Heart Rate Variability in a Cross-Sectional Occupational Sample Evidence for Impaired Vagal Control", The Clinical Journal of Pain, Publish Ahead of Print, (2015), 31 pgs
4. STAUD, ROLAND "Heart rate variability as a biomarker of fibromyalgia syndrome", Fut Rheumatol 3 (5) - NIH Public Access, (10/01/08), 475-483
5. CINAZ, BURCU, et al., "Monitoring of mental workload levels during an everyday life office-work scenario", Pers Ubiquit Comput 17, (2013), 229-239
6. SAY, MUSA, et al., "Responses of Heart Rate Variability to Acute Pain After Minor Spinal Surgery: Optimal Thresholds and Correlation With the Numeric Rating Scale", J Neurosurg Anesthesiol, Vol. 00, No. 00 (2014), 1-7
7. HALLMAN, DAVID M., et al., "Changes in physical activity and heart rate variability in chronic neck-shoulder pain: monitoring during work and leisure time", Int Arch Occup Environ Health 87, (2014), 735-744
8. ZHANG, JOHN, "Effect of Chiropractic Care on Heart Rate Variability and Pain in a Multisite Clinical Study", Jimmal of Manipulative and Physiological Therapeutics, Vol. 29, No. 4, (2006), 267-274
9. WILLIAMS, DEWAYNE P., et al., "Effects of Chronic Pelvic Pain on Heart Rate Variability in Women", The Journal of Urology, Vol. 194,, (November 2015), 1-6

TABLE 3-continued

References cited in Table 1.

10 EVANS, SUBHADR, et al., "Heart rate variability as a bimarker for autonomic nervous system response differences between children with chronic pain and healthy control children", Journal of Pain Research 3.6, (2013), 449-457
11 VILLAREJO, VIQUEIRA MARIA, et al., "A Stress Sensor Based on Galvanic Skin Response (GSR) Controlled by ZigBee", Sensors 12, (2012), 6075-6101
12 STORM, H., et al., "Skin conductance correlates with perioperative stress", Acta Anaesthesiol Scand 46, (2002), 887-895
13 BAKKER JORN, et al., "What's your current stress level? Detection of stress patterns from GSR sensor data", Eindhoven University of Technology - The Netherlands, (2011), 1-8
14 LIDBERG, LARS, et al., "Sympathetic Skin Nerve Discharges in Relation lo Anipliliule ol Skin Resistance Responses", Psychophysiology, Vol. 18, No. 3, (May 1980, 268-270
15 G, CHIUNG-CHENG, et al., "Photoplethysmography variability as an alternative approach to obtain heart rate variability information in chronic pain patient", J Clin Monit Comput - Published online, (02/24/15), 1-6
16 HALLMAN, DAVID M., et al., "Changes in physical activity and heart rate variability in chronic neck-shoulder pain: monitoring during work and leisure time", Int Arch Occup Environ Health 87, (2014), 735-744
17 BOSELLI, E., et al., "Prediction of immediate postoperative pain using the analgesia/ nociception index: a prospective observational study", British Journal of Anaesthesia 112 (4):, (2014), 715-721
18 BEN-ISRAEL, NIR, et al., "Monitoring the nociception level: a multi-parameter approach", J Clin Monit Comput 27, (2013), 659-668
19 HALLMAN, DAVID M., et al., "Changes in physical activity and heart rate variability in chronic neck-shoulder pain: monitoring during work and leisure time", Int Arch Occup Environ Health 87, (2014), 735-744
20 WONG, JIH-SEN, et al., "A comparative study of pulse rate variability and heart rate variability in healthy subjects", J Clin Monit Comput 26, (2012), 107-114
21 CHUANG, CHIUNG-CHENG, et al., "Photoplethysmography variability as an alternative approach to obtain heart rate variability information in chronic pain patient", J Clin Monit Coniput - Published online, 02/24/15), 1-6
22 SACCO, MARCELLA, et al., "The Relationship Between Blood Pressure and Pain", The Journal of Clinical Hypertension Vol. 15, No 8, (August 2013), 600-605
23 STORM, H., et al., "Skin conductance correlates with perioperative stress", Acta Anaesthesiol Scand 46, (2002), 887-895
24 KOENIG, JULIAN, et al., "Chronic Pain and Heart Rate Variability in a Cross-Sectional Occupational Sample Evidence for Impaired -Vagal Control", The Clinical Journal of Pain, Publish Ahead of Print, (2015), 31 pgs
25 ZAMUNER, A, R., et al., "Relationship between sympathetic activity and pain intensity in fibromyalgia", Clin Exp Rheumatol 33 - Abstract, [Online]. Retrieved from the Internet: <URL: http://www.ncbi.nlm.nih.gov.ezp3.lib.umn.edu/pubmed/25786044, (February 2015), 1-2
26 VAN VELZEN, MARIT H.N., et al,, "Effect of heat-induced pain stimuli on pulse transit time and pulse wave amplitude in healthy volunteers", Physiological Measurement 37, (2016), 52-66
27 KIM, YOUNG UK, et al., "Pulse Transit Time as a Predictor of the Efficacy of a Celiac Plexus Block in Patients With Chronic Intractable Abdominal Pain", Clin J Pain, Vol. 32, No. 6, (June 2015), 522-526
28 KANG, JON-EUN, et al., "Pulse transit time shows vascular changes caused by propofol in children", J Clin Monit Comput 29, (2015), 533-537
29 BANOS, ORESTI, et al., "PhysioDroid: Combining Wearable Health Sensors and Mobile Devices for a Ubiquitous, Continuous, and Personal Monitoring", The Scientific World Journal, Vol. 2014 Article ID 190824, (2014), 11 pgs
30 ZAMUNER, A. R., et al., "Relationship between sympathetic activity and pain intensity in fibromyalgia", Clin Exp Rheumatol 33 - Abstract, [Online]. Retrieved from the Internet: <URL: http://www.ncbi.nlm.nih.gov.ezp3.lib.umn.edu/pubmed/25786044, (February 2015), 1-2
31 LEDOWSKI, THOMAS, et al., "The influence of age and sex on the relationship between heart rate variability, haemodynamic variables and subjective measures of acute post-operative pain", European Journal of Anaesthesiology, Vol. 28, No. 6, (2011), 433-437
32 CHAPMAN, C. RICHARD, et al., "Phasic pupil dilation response to noxious stimulation in normal volunteers: relationship to brain evoked potentials and pain report", (1999), 44-52
33 ARSENAULT, MARIANNE, et al., "Pain Modulation Induced by Respiration: Phase and Frequency Effects", Neuroscience 252, (2013), 501-511
34 STURGEON, JOHN A., et al., "Respiratory Sinus Arrhythmia: a Marker of Resilience to Pain Induction", Int J. Behav. Med. 21 (2014), 961-965
35 ZAMUNER, ANTONIO R., et al., "Respiratory Sinus Arrhythmia and its Association with Pain in Women with Fibromyalgia Syndrome", Pain Practice, Vol. 16, Issue 6, (2016), 704-711
36 KODITUWAKKU, SANDIJN, et al., "Point Process Respiratory Sinus Arrhythmia Analysis during Deep Tissue Pain Stimulation", Computing in Cardiology 38, (2011), 193-196
37 LANE, JAMES D., et al., "Respiratory Sinus Arrhythmia and Cardiovascular Responses to Stress", Psychophysiology, Vol. 29, No. 4, (1992), 461-470

TABLE 3-continued

References cited in Table 1.

| | |
|---|---|
| 38 | DUSCHEK, S., "Relationship between baroreceptor cardiac reflex sensitivity and pain experience in normotensive individuals", International journal of Psychophysiology 65, (2007), 193-200 |
| 39 | SWENNE, C. A., "Baroreflex sensitivity: mechanisms and measurement", Neth Heart J 21, (2013), 58-60 |
| 40 | Anderson. (2016). Utility of baroreflex sensitivity as a marker of stress. |
| 41 | CHUNG, OK Y., "Baroreflex sensitivity associated hypoalgesia in healthy states is altered by chronic pain", Pain 138, (2008), 87-97 |
| 42 | GOUVEIA, S., et al., "Assessing Baroreflex Sensitivity in the Sequences Technique: Local versus Global Approach", Computers in Cardiology, 32, (2005), 279-282 |
| 43 | Parlow et al (1995). Spontaneous cardiac baroreflex in humans: comparison with drug-induced responses |
| 44 | Hayano & Yasuma 2003). Hypothesis: respiratory sinus arrhythmia is an intrinsic resting function of cardiopulmonary system. |
| 45 | Heffernan et al. (2007). Arterial stiffness and baroreflex sensitivity following bouts of aerobic and resistance exercise. |
| 46 | Ogoh et al. (2005). Autonomic nervous system influence on arterial baroreflex control of the heart rate during exercise in humans. |
| 47 | Sabharwal et al. (2016). Exercise prevents development of autonomic dysregulation and hyperalgesia in a mouse model of chronic muscle pain. |
| 48 | LEE, JIHYOUNG, et al., "Validation of normalized pulse volume in the outer ear as a simple measure of sympathetic activity using warm and cold pressor tests: towards applications in ambulatory monitoring", Physiol. Meas. 34, (2013), 359-375 |
| 49 | SAWADA, YUKIHIRO, et al., "Normalized pulse volume (NPV) derived photo-plethysmography as a more valid measure of the finger vascular tone", International Journal of Psychophysiology 41, (2001), 1-10 |
| 50 | BARKLEY, JACOB E., et al., "The effect of spinal cord stimulation unit revision on perceived pain, anxiety, mobility and physical activity in individuals with low back/lower extremity pain", Kent State University - The Spine and Pain Institute, 1 pg. (12/11/2014) |
| 51 | DANSIE, ELIZABETH J., et al., "Activity in Adults with Chronic Widespread Pain", The Journal of Pain - Accepted Manuscript, (2014), 33 pgs |
| 52 | SATO, KARINA L/, et al., "Spinal Cord Stimulation (SCS) Improves Decreased Physical Activity Induced by Nerve Injury", Behavioral Neuroscience, Vol. 128, No. 5, (2014), 625-632 |
| 53 | KEEFE, FRANCIS J,, et al., "An Objective Approach to Quantifing Pain Behavior and Gait Patterns in Low Back Pain Patients", Pain, 21, (1985), 153-161 |
| 54 | LAMOTH, CLAUDINE J.C., et al., "Pelvis-Thorax Coordination in the Transverse Plane During Walking in Persons With Nonspecific Low Back Pain", SPINE, Vol. 27, No. 4, (2002), E92-E99 |
| 55 | LAMOTH, CLAUDINE J.C., et al., "How do persons with chronic low back pain speed up and slow down? Trunk-pelvis coordination and erector spinae activity during gait", Gait & Posture 23, (2006), 230-239 |
| 56 | SIMOES, MARIO A., "Feasibility of Wearable Sensors to Determine Gait Parameters", University of South Florida Scholar Commons, (2011), 1-98 |
| 57 | DE-LA-HERRAN, ALVARO M., et al., "Gait Analysis Methods: An Overview of Wearable and Non-Wearable Systems, Highlighting Clinical Applications", Sensors 14, (2014), 3362-3394 |
| 58 | TAO, WEIJUN, et al., "Gait Analysis Using Wearable Sensors", Sensors 12, (2012), 2255-2283 |
| 59 | CHENG, QIAN, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), September 25th, 2013,, (2013), 1-10 |
| 60 | ALLUM, JOHN H.J., et al., "A speedy solution for balance and gait analysis: angular velocity measured at the centre of body mass", Current Opinion in Neurology 18, (2005), 15-21 |
| 61 | ZHOU, JING, et al., "Recurrent Convolutional Neural Network Regression for Continuous Pain Intensity Estimation in Video", Technical Report, (05/03/16), 1-11 |
| 62 | SAYAR, KEMAL, et al., "Sleep Quality in Chronic Pain Patients", Can J. Psychiatry, Vol. 47, No. 9, (November 2002), 844-848 |
| 63 | PALERMO, TONYA M., et al., "Subjective Sleep Disturbances in Adolescents With Chronic Pain: Relationship to Daily Functioning and Quality of Life", The Journal of Pain, Vol. 6, No. 3, (March 2995), 201-207 |
| 64 | ARTNER, JURAJ, et al., "Prevalence of sleep deprivation in patients with chronic neck and back pain: a retrospective evaluation of 1016 patients", Journal of Pain Research: 6, (2013), 1-6 |
| 65 | RAMINEN, TINA, et al., "The Impact of Spinal Cord Stimulation on Sleep Patterns", Neuromodulation 19, (2016), 477-481 |
| 66 | PALERMO, TONYA M., et al., "Subjective Sleep Disturbances in Adolescents With Chronic Pain: Relationship to Daily Functioning and Quality of Life", The Journal of Pain, Vol. 6, No. 3, (March 2005), 201-207 |
| 67 | CINAZ, BURCU, et al., "Monitoring of mental workload levels during an everyday life office-work scenario", Pers Ubiquit Comput 17, (2013), 229-739 |
| 68 | BAKKER, JORN, et al., "What's your current stress level? Detection of stress patterns from GSR sensor data", Eindhoven University of Technology - The Netherlands, (2011), 1-8 |

TABLE 3-continued

References cited in Table 1.

69 ALO, KENNETH M., et al., "Effect of Spinal Cord Stimulation on Sensory Nerve Conduction Threshold Functional Measures", Neuromodulation, Volume 3, Number 3, (2000), 145-154
70 KEMLER, MARIUS A., et al., "Impact of Spinal Cord Stimulation on Sensory Characteristics in Complex Regional Pain Syndrome Type 1 - A Randomized Trial", Anesthesiology, 95, (2001), 72-80
71 EISENBERG, ELON, et al., "Quantitative Sensory Testing for Spinal Cord Stimulation in Patients With Chronic Neuropathic Pain", (2006), 161-165
72 MIRONER, Y. EUGENE, et al., "Pain Tolerance Threshold: A Pilot Study of an Objective Measurement of Spinal Cord Stimulator Trial Results", Pain Medicine, Vol. 1, No. 2, (2000), 110-115
73 MAUER, C,, et al., "Quantitative sensory testing in the German Research Network on Neuropathic Pain (DFNS): Somatosensory abnormalities in 1236 patients with different neuropathic pain syndromes", Pain 150, (2010), 439-450
74 RASCHE, DIRK, et al., "Quantitative Sensory Testing in Patients With Chronic Unilateral Radicular Neuropathic Pain and Active Spinal Cord Stimulation", Neuromodulation, Vol. 9, No. 3, (2006), 239-247
75 PLEGER, BURKHARD, et al., "Patterns of cortical reorginization parallel impaired tactile discrimination and pain intensity in complex regional pain syndrome", NeuroImage 32, (2006), 503-510
76 MOSELEY, G. LORIMER, et al., "Tactile Discrimination, but not tactile stimulation alone, reduces chronic lima pain", Pain 137, (2008), 600-608
77 SCHULZ, ENRICO, et al., "Prefrontal Gamma Oscillations Encode Tonic Pain in Humans", Cerebral Cortex 2015, (03/08/15), 1-8
78 PRICHEP, LESLIE S., et al., "Evaluation of the Pain Matrix Using EEG Source Localization: A Feasibility Study", Pain Medicine 12, (2011), 1241-1248
79 SCHULZ, ENRICO, et al., "Prefrontal Gamma Oscillations Encode Tonic Pain in Humans", Cerebral Cortex 2015, (03/08/15), 1-8
80 SARNTHEIN, JOHANNES, et al., "Increased EEG power and slowed dominant frequncy in patients with neurogenic pain", Brain 129, (2005), 55-64
81 THEUVENEL, PETER J., et al., "Responses to Median and Tbial Nerve Stimulation in Patients with Chronic Neuropathic Pain", Brain Topography, Vol. 11, No. 4, (1999), 306-313
82 GRANOVSKY, YELENA, et al., "Objective Correlate of Subjective Pain Perception by Contact Heat-Evoked Potentials", The Journal of Pain, Vol. 9, No. 1, (January 2008), 53-63
83 PLUIJMS, WOUTER A., et at., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.
84 GRANOVSKY, YELENA, et al., "Objective Correlate of Subjective Pain Perception by Contact Heat-Evoked Potentials", The Journal of Pain, Vol. 9, No. 1, (January 2008), 53-63
85 CIAMPI DE ANDRADE, DANIEL, et al, "Neurophysiological assessment of spinal cord stimulation in failed back surgery syndrome", Pain 150, (2010), 485-491
86 Hodges et al. (1996). Inefficient muscular stabilization of the lumbar spine associated with low back pain: a motor control evaluation of Transversus Abdominis.
87 AHERN, DAVID K., et al., "Comparison of lumbar paravertebral EMG patterns in chronic low back pain patients and non-patient controls", Pain, 34, (1988), 153-160
88 PANJABI, MANOHAR, "Clinical spinal instability and low back pain", Journal of Electromyography and Kinesiology 13, (2003), 371-379
89 NEBLETT, RANDY, et al., "What Is The Best Surface EMG Measure of Lumbar Flexion-Relation for Distinguishing Chronic Low Back Pain Patients From Pain-Free Controls?", Clin J Pain 29 (4) - NIH Public Access, (April 2013), 334-340
90 BENECK, GEORGE J., et al., "Spectral analysis of EMG using intramuscular electrodes reveals non-linear fatigability characteristics in persons with chronic low back pain", Journal of Electromyography and Kinesiology 23, (2013), 70-77
91 GEISSER, MICHAEL E., et al., "Pain-Related Fear, Lumbar Flexion, and Dynamic EMG Among Persons With Chronic Musculoskeletal Low Back Pain", Clin J Pain, Vol. 20, No. 2, (April 2004)
92 WONG, ARNOLD Y.L., et al., "Does experimental low back pain change posteroanterior lumbar spinal stiffness and trunk muscle activity? A randomized crossover study", Clinical Biornechanics 34, (2016), 45-52
93 WILLER, JEAN CLAUDE, "Comparative Study of Perceived Pain and Nociceptive Flexion Reflex in Man", Pain, 3, (1977), 69-80
94 CHAN, C. W.Y., et al., "Subjective pain sensation is linearly correlated with the Flexion reflex in man", Brain Research, 479, (1989), 145-150
95 RHUDY, JAMIE L., et al., "Defining the nociceptive flexion reflex (NFR) threshold in human participants: A comparison of different scoring criteria", Pain 128, (2007), 244-253
96 SKLJAREVSKI, V., et al., "The nociceptive flexion reflex in humans - review article", Pain, 96, (2002), 3-8
97 MYLIUS, VETT, et al,, "Sex differences in nociceptive withdrawal reflex and pain perception", Somatosensory and Motor Research 22 (3), (September 2005), 207-211
98 GREEN, ALEXANDE L., "Measurement of muscle sympathetic nerve activity reveals true sympathetic changes in chronic pain", Exp Physiol 97.10, (2012), 1083

TABLE 3-continued

References cited in Table 1.

99 FAZALBHOY, AZHARUDDIN, et al., "Individual differences in the cardiovascular responses to tonic muscle pain: parallel increases or decreases in muscle sympathetic nerve activity, blood pressure and heart rate", Exp Physiol 97.10, (2012), 1084-1092.

100 KOENIG, J., et al., "Heart rate variability and experimentally induced pain in healthy adults: A systematic review", European Journal of Pain 18, (2014), 301-314

101 ZAMUNÉR, A. R., et al., "Relationship between sympathetic activity and pain intensity in fibromyalgia", Clin Exp Rheumatol 33 - Abstract, [Online]. Retrieved from the Internet: <URL: http://www.nchi.nlm.nih.gov.ezp3.lib.umn.edu/pubmed/25786044, (February 2015), 1-2

102 BALIKI, MARWAN N., et al., "Beyond Feeling: Chronic Pain hurts the Brain, Disrupting the Default-Mode Network Dynamics", The Journal of Neuroscience, 28 (6), (02/06/08), 1398-1403

103 TAGLIAZUCCHI, ENZO, et al., "Brain resting state is disrupted in chronic back pain patients", Neurosci Lett. 485 (1) - NIH Public Access, (11/12/10), 26-31

104 SMALLWOOD, RACHEL F., et al., "Structural Brain Anomalies and Chronic Pain: A Quantitative Meta-Analysis of Gray Matter Volume", The Journal of Pain, Vol. 14, No, 7, (July 2013), 663-675

105 BARAD, MEREDITH J., et al., "Complex Regional Pain Syndrome Is Associated With Structural Abnormalities in Pain-Related Regions of the Human Brain", The Journal of Pain, Vol. 15, No. 2, (February 2014), 197-203

106 SCHULMAN, JOSHUA J., et al., "Thalamocortical dysrhythmia syndrome: MEG imaging of neuropathic pain", (07/25/14), 33-39

107 WALTON, K. D., et al., "Abnormal thalamocortical activity in patients with Complex Regional Pain Syndrome (CRPS) Type 1", Pain 150, (2010), 41-51

108 SIDDALL, PHILLIP J., et al., "Magnetic Resonance Spectroscopy Detects Biochemical Changes in the Brain Associated with Chronic Low Back Pain: A Preliminary Report", Anesth Analg 102, (2006), 1164-1168

109 UCEYLER, NUNCAN, et al., "Differential expression of cytokines in painful and painless neuropathies", (2007)

110 PLAZA-MANZANO, GUSTAVO, et al., "Changes in Biochemical Markers of Pain Perception and Stress Response After Spinal Manipulation", Journal of Orthopaedic & Sports Physical Therapy, Vol. 44, No. 4, (April 2014), 231-239

111 PATTI, GARY J., et al., "Metabolomics implicates altered sphingolipids in chronic pain of neuropathic origin", nature chemical biology, Vol. 8, (March 2012), 232-234

112 McGregor et al. (2011). The biochemistry of chronic pain and fatigue

113 KESHARI, KAYVAN R., et al., "Lactic Acid and Proteoglycans as Metabolic Markers dor Discogenic Back Pain", SPINE, Vol. 13, No. 3, (2008), 312-317

114 C.O. Stiller et al. (1996) Release of GABA in dorsal horn and suppression of tactile allodynia by SCS in mononeurophathic rats.

115 TAUDA, MAKOTO, et al., "P2X4 receptors and neuropathic pain", Frontiers in Cellular Neuroscience, Vol. 7, Article 191, (10/28/13), 1-6

116 Symons, Frank J., Issam ElGhazi, Brian G. Reilly, Chantel C. Barney, Leah Hanson, Angela Panoskaltsis-Mortari, Ian M. Armitage, and George L. Wilcox. "Can biomarkers differentiate pain and no pain subgroups of nonverbal children with cerebral palsy? A preliminary investigation based on noninvasive saliva sampling." Pain Medicine 16, no. 2 (2015): 249-256.

117 Generaal, Ellen, Nicole Vogelzangs, Gary J. Macfarlane, Rinie Geenen, Johannes H. Smit, Brenda WJH Penninx, and Joost Dekker. "Reduced hypothalamic-pituitary-adrenal axis activity in chronic multi-site musculoskeletal pain: partly masked by depressive and anxiety disorders." BMC Musculoskeletal disorders 15, no. 1 (2014): 227.

118 McBeth, John, Yee H. Chiu, Alan J. Silman, David Ray, Richard Morriss, Chris Dickens, Anindya Gupta, and Gary J. Macfarlane. "Hypothalamic-pituitary-adrenal stress axis function and the relationship with chronic widespread pain and its antecedents." Arthritis research & therapy 7, no. 5 (2005): R992.

119 McCarthy, K. F., and C. McCrory. "Cerebrospinal fluid levels of glial cell-derived neurotrophic factor correlate with spinal cord stimulation frequency in patients with neuropathic pain: a preliminary report" Spinal cord 52 (2014): S8-S10.

120 Marchi, Antonio, Renato -Vellucci, Sergio Mameli, Anna Rita Piredda, and Gabriele Finco. "Pain biomarkers." Clinical drug investigation 29 (2009): 41.

121 Denk, Franziska, and Stephen B. McMahon "Chronic pain: emerging evidence for the involvement of epigenetics." Neuron 73, no. 3 (2012): 435-444.

122 Latremoliere, Alban, Alexandra Latini, Nick Andrews, Shane J. Cronin, Masahide Fujita, Katarzyna Gorska, Ruud Hovius et al. "Reduction of neuropathic and inflammatory pain through inhibition of the tetrahydrobiopterin pathway." Neuron 86, no. 6 (2015): 1393-1406.

123 Čulić, Ognjen, Mario D. Cordero, Tihana Žanić-Grubišić, Anita Somborac-Bačura, Lara Batičić Pučar, Dijana Detel, Jadranka Varljen, and Karmela Barišić. "Serum activities of adenosine deaminase, dipeptidyl peptidase IV and prolyl endopeptidase in patients with fibromyalgia: diagnostic implications." Clinical rheumatology 35, no. 10 (2016): 2565-2571,

What is claimed is:

1. A method for managing pain of a patient, comprising:
receiving multiple parameters related to the pain;
receiving weighting factors;
generating a quantitative measure of the pain automatically using a processor, the generation including adjusting the weighting factors by automatic adaptation to the patient over time, producing weighted multiple parameters by applying a weighting factor of the adjusted weighting factors to each parameter of the multiple parameters, producing a signal metric using the weighted multiple parameters, and determining the quantitative measure of the pain using the signal metric;
delivering one or more pain-relief therapies using a pain relief device; and
controlling the delivery of the one or more pain-relief therapies based on the quantitative measure of the pain.

2. The method of claim 1, wherein the generating the quantitative measure of the pain and the controlling the delivery of the one or more pain-relief therapies are performed using a portable device wirelessly coupled to the pain relief device.

3. The method of claim 2, further comprising managing the pain of the patient remotely through a network, including:
producing a notification based on the quantitative measure of the pain using the portable device;
transmitting the notification to the network using the portable device; and
receiving commands for adjusting the delivery of the one or more pain-relief therapies from the network using the portable device.

4. The method of claim 2, wherein delivering the one or more pain-relief therapies using the pain relief device comprises delivering spinal cord stimulation using an implantable medical device.

5. The method of claim 2, wherein delivering the one or more pain-relief therapies using the pain relief device comprises delivering deep brain stimulation using an implantable medical device.

6. The method of claim 1, wherein the multiple parameters comprise one or more mental state parameters indicative of the patient's mental state related to the pain.

7. The method of claim 6, further comprising determining the one or more mental state parameters using an input from the patient.

8. The method of claim 6, further comprising determining the one or more mental state parameters using one or more measures of the patient's neural activity sensed using one or more sensors.

9. The method of claim 1, wherein the multiple parameters comprise time of day.

10. The method of claim 1, wherein the multiple parameters comprise one or more environmental parameters including at least one of temperature, humidity, or air pressure.

11. A system for managing pain of a patient using a network, comprising:
a pain analyzer configured to receive multiple parameters related to the pain, to receive weighting factors, to adjust the weighting factors by automatic adaptation to the patient over time, to produce weighted multiple parameters by applying a weighting factor of the adjusted weighting factors to a parameter of the multiple parameters, to produce a signal metric using the weighted multiple parameters, and to generate a quantitative measure of the pain using the signal metric;
a pain relief device configured to deliver one or more pain-relief therapies; and
a control circuit configured to control the delivery of the one or more pain-relief therapies based on the quantitative measure of the pain.

12. The system of claim 11, comprising a portable device including at least the pain analyzer.

13. The system of claim 12, wherein the portable device comprises a hand-held or wearable device and is configured to:
produce a notification based on the quantitative measure of the pain;
transmit the notification to the network; and
receive commands for adjusting the delivery of the one or more pain-relief therapies from the network.

14. The system of claim 13, wherein the portable device comprises a smartphone, a laptop computer, or a tablet computer.

15. The system of claim 12, comprising an implantable medical device configured to be wirelessly coupled to the portable device, the implantable medical device including at least the pain relief device.

16. The system of claim 15, further comprising:
one or more sensors configured to sense one or more signals from the patient;
one or more sensing circuits configured to process the sensed one or more signals; and
one or more parameter generators configured to generate one or more parameters of the multiple parameters.

17. The system of claim 11, wherein the pain analyzer is configured to receive one or more mental state parameters of the multiple parameters, the one or more mental state parameters indicative of the patient's mental state related to the pain.

18. The system of claim 11, wherein the pain analyzer is configured to receive a time of day of the multiple parameters and to produce the signal metric by including circadian influence on the pain.

19. The system of claim 11, wherein the pain analyzer is configured to receive one or more environmental parameters of the multiple parameters, the environmental parameters including at least one of temperature, humidity, or air pressure.

20. A non-transitory computer-readable storage medium including instructions, which when executed by a system, cause the system to perform a method for managing pain of a patient, the method comprising:
receiving multiple parameters related to the pain;
receiving weighting factors;
generating a quantitative measure of the pain automatically using a processor, the generation including adjusting the weighting factors by automatic adaptation to the patient over time, producing weighted multiple parameters by applying a weighting factor of the adjusted weighting factors to each parameter of the multiple parameters, producing a signal metric using the weighted multiple parameters, and determining the quantitative measure of the pain using the signal metric; and
controlling delivery of one or more pain-relief therapies from a pain-relief device based on the quantitative measure of the pain.

* * * * *